United States Patent [19]

Klessing

[11] Patent Number: 4,535,158

[45] Date of Patent: Aug. 13, 1985

[54] OPTIONALLY N-SUBSTITUTED AMINODESOXY-1.4;3.6-DIANHYDROHEXITOL DERIVATIVES

[75] Inventor: Klaus Klessing, Ettlingen, Fed. Rep. of Germany

[73] Assignee: Willmar Schwabe GmbH & Co., Karlsruhe, Fed. Rep. of Germany

[21] Appl. No.: 533,538

[22] Filed: Sep. 19, 1983

Related U.S. Application Data

[62] Division of Ser. No. 285,358, Jul. 20, 1981, Pat. No. 4,413,122.

[30] Foreign Application Priority Data

Jul. 25, 1980 [DE] Fed. Rep. of Germany ....... 3028288

[51] Int. Cl.³ ................ C07D 473/08; C07D 473/10; C07D 473/34; C07D 493/04
[52] U.S. Cl. .................................... 544/118; 544/264; 544/265; 544/268; 544/277
[58] Field of Search ............... 544/118, 264, 265, 268, 544/277

[56] References Cited

U.S. PATENT DOCUMENTS 4,479,951 10/1984 Klessing et al. .................... 544/268

FOREIGN PATENT DOCUMENTS 1090358 11/1967 United Kingdom .

OTHER PUBLICATIONS

European Patent Application, 44927, 2-3-1982.

*Primary Examiner*—Robert W. Ramsuer
*Attorney, Agent, or Firm*—Toren, McGeady, Stanger, Goldberg & Kiel

[57] ABSTRACT

Aminodesoxy-1.4;3.6-dianhydrohexitol derivatives of the general formula I,

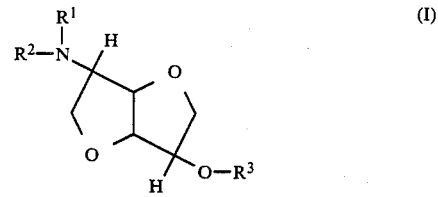

wherein $R^1$ and $R^2$ in each case independently of one another, signifies a hydrogen atom or a lower alkyl group with 1 to 4 C-atoms or wherein $R^1$ signifies a hydrogen atom and $R^2$ an adamant(1)yl radical or wherein $R^1$, and $R^2$, together with the nitrogen atom to which they are attached, (a) signify the residue of a cyclic, non-aromatic secondary amine possibly containing a further hetero atom or (b) the aden(9)yl radical possibly mono- or disubstituted on the 6-amino group or (c) the 6-alkylmercaptopurin(9)yl radical or (d) the theophyllin-(7)yl radical or (e) the 6-chloropurin-9-yl radical or wherein $R^1$ signifies a hydrogen atom or a lower alkyl group with 1 to 4 C-atoms and $R^2$ an ω-theophyllin(7)ylalkyl radical or an ω-theobromin-1-ylalkyl radical or an ω-(N,N′-di-lower alkyl-substituted xanthin-N″-yl)alkyl radical, whereby "lower alkyl" signifies an alkyl group with 1 to 5 C-atoms, or an ω-adenin-9-ylalkyl radical, whereby the alkyl radical has 2 to 7 C-atoms and can be straight-chained or branched, and wherein $R^3$ signifies a hydrogen atom, a methanesulphonyl or toluenesulphonyl group, as well as their acid-addition salts.

Processes for the preparation of said compounds and use of said compounds as reactive intermediate products for the preparation of the corresponding pharmacologically-effective amino-desoxy-1.4;3.6-dianhydrohexitol nitrates.

43 Claims, No Drawings

OPTIONALLY N-SUBSTITUTED AMINODESOXY-1.4;3.6-DIANHYDROHEXITOL DERIVATIVES

This is a divisional application of application Ser. No. 285,358, filed July 20, 1981, now U.S. Pat. No. 4,413,122.

The invention concerns aminodesoxy-1.4;3.6-dianhydrohexitol derivatives of the general formula I,

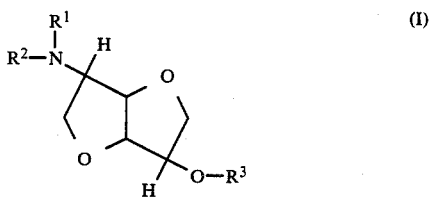
(I)

wherein $R^1$ and $R^2$, in each case independently of one another, signify a hydrogen atom or a lower alkyl group with 1 to 4 C-atoms, or wherein $R^1$ signifies a hydrogen atom and $R^2$ an adamant(1)yl radical or wherein $R^1$ and $R^2$, together with the nitrogen atom to which they are attached signify (a) the residue of a cyclic, non-aromatic secondary amine possibly containing a further hetero atom or (b) the aden(9)yl radical possibly mono- or disubstituted on the 6-amino group or (c) the 6-alkylmercaptopurin(9)yl radical or (d) the theophyllin(7)yl radical or (e) the 6-chloropurin(9)yl radical or wherein $R^1$ signifies a hydrogen atom or a lower alkyl group with 1 to 4 C-atoms and $R^2$ an ω-theophyllin(7)ylalkyl radical or an ω-theobrom-1-ylalkyl radical or an ω-(N,N'-di-lower alkyl-substituted xanthin-N''-yl) radical, whereby "lower alkyl" signifies an alkyl group with 1 to 5 C-atoms, or an ω-adenin-9-ylalkyl radical, whereby the alkyl radical in each case has 2 to 7 C-atoms and can be straight-chained or branched, and wherein $R^3$ signifies a hydrogen atom, a methanesulphonyl or toluenesulphonyl group, as well as their acid-addition salts.

The basic structure of these compounds consists of one of the stereoisomeric 1.4;3.6-dianhydrohexitols, which can be converted into one another by epimerisation, namely, either 1.4;3.6-dianhydro-L-iditol (="isodide") (II)

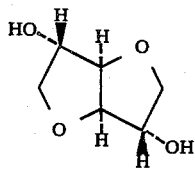
(II)

in which the OH groups in the 2- and 5-position each have the exo-configuration, or 1.4;3.6-dianhydro-D-glucitol (="isosorbide") (III)

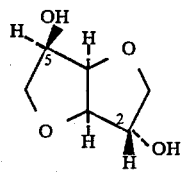
(III)

which has an exo-standing and an endo-standing OH group and thus—in the case of various substituents in the 2- and 5-position—occurs in two isomeric forms.

Finally, the basic structure of some compounds consists of 1.4;3.6-dianhydro-D-mannitol (="isomannide") (IV)

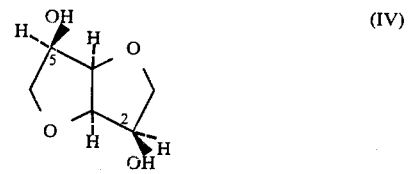
(IV)

which has two endo-standing OH groups.

Since, in contradistinction to the glucitol derivatives, in the case of the iditol and mannitol derivatives a difference between the 2- and 5-substituents is not possible because the $C^2$-atom, in the case of rotating the molecule through 180°, becomes the $C^5$-atom, references to the 5-position or 2-position of substituents is superfluous in the case of these derivatives. However, for the sake of a better comparison of the structures of the individual compounds with the general formulae, the isodide derivatives are always referred to as 5-aminoisodide derivatives since they result from the isosorbide derivatives acyl-substituted in the 5-position. Correspondingly, the isomannide acyl derivatives employed as starting compounds are referred to as 2-acylisomannide derivatives since the 2-aminoisosorbide derivatives are prepared from them.

A brief summary regarding the stereoisomerism of the 1.4;3.6-dianhydrohexitols is given by J. A. Mills in Advances in Carbohydrate Chem. 10, 1–53 (1955).

The compounds according to the invention are valuable intermediates for the preparation of the possibly N-substituted aminodesoxy-1.4;3.6-dianhydrohexitol mononitrates of the general formula (Ia),

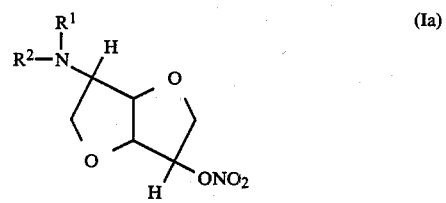
(Ia)

wherein $R^1$ and $R^2$ possess the above-mentioned meanings, described in the three simultaneously filed German Patent Application Nos. P 30 28 272.5, P 30 28 273.6 and P 30 28 340.0.

The compounds of general formula (Ia) possess coronary flowthrough-increasing, spasmolytic, blood pressure-lowering, negative inotropic and heart frequency-reducing effectiveness. They are suitable for the treatment of coronary diseases, for the treatment and prophylaxis of angina pectoris attacks, for the post-treatment of heart infarcts and for the treatment of heart insufficiencies. Furthermore, they bring about an improvement of the peripheral blood flow and of the blood flow in the brain.

Since it has been shown that, for example, the 2- and 5-mononitrates as well as the 2,5-dinitrate of isosorbide, known from U.S. Pat. No. 3,886,186, which are also pharmacologically-effective substances with haemodynamic, vasodilatory and antianginous effectiveness, bring about unpleasant side effects, especially headaches, some of which are poorly resorbable and some of which—since, in the case of the dinitrates, they are explosive materials—can only be prepared and handled under special precautionary conditions, there exists a need for the making available of new pharmaceutical agents with the same activity spectrum, which do not display the disadvantages of the known isosorbide mononitrates (ISMN) and of isosorbide dinitrate (ISDN), as well as for the provision of new 1.4;3.6-dianhydrohexitol mononitrates which can be used as active compounds of such pharmaceutical agents.

The task forming the basis of the invention consists in satisfying the mentioned need, the solution of this problem in making available the compounds according to the invention as reactive intermediate products for the preparation of the new 1.4;3.6-dianhydrohexitol mononitrates.

Consequently, the subject of the invention are 1. 5-amino-5-desoxy-1.4;3.6-dianhydro-L-iditol derivatives of the general formula V,

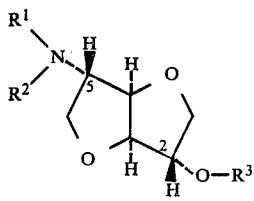
(V)

wherein $R^1$, $R^2$ and $R^3$ possess the meanings mentioned in claim 1, as well as their acid-addition salts;

2. 5-amino-5-desoxy-1.4;3.6-dianhydro-D-glucitol derivatives of the general formula VI

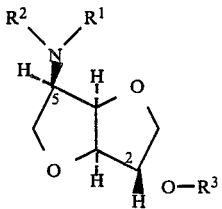
(VI)

wherein $R^1$, $R^2$ and $R^3$ possess the meanings mentioned in claim 1, as well as their acid-addition salts;

3. 2-amino-2-desoxy-1.4;3.6-dianhydro-D-glucitol derivatives of the general formula VII,

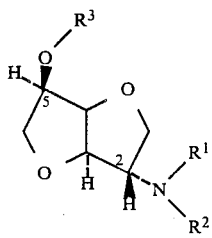
(VII)

wherein $R^1$, $R^2$ and $R^3$ possess the meanings mentioned in claim 1, as well as their acid-addition salts;

4. 2-amino-2-desoxy-1.4;3.6-dianhydro-D-mannitol derivatives of the general formula VIII

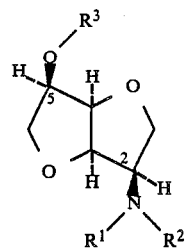
(VIII)

wherein $R^1$, $R^2$ and $R^3$ possess the meanings mentioned in claim 1, as well as their acid-addition salts;

5. (purin-9-yl)-desoxy-1.4;3.6-dianhydrohexitol derivatives of the general formula IX

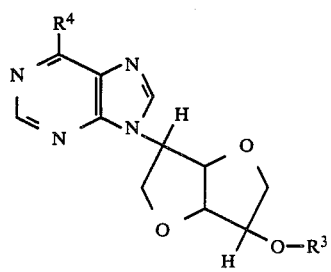
(IX)

wherein $R^3$ signifies a hydrogen atom, a methanesulphonyl or toluenesulphonyl group and $R^4$ an amino, alkylmercapto, alkylamino or dialkylamino group with 1 to 4 C-atoms, an $\omega$-phenylalkyl amino group, the alkyl radical of which has 1 to 8 C-atoms and the phenyl radical of which is possibly halogen-substituted, or the radical of a cyclic, non-aromatic, secondary amine possibly containing a further hetero atom, or a chlorine atom, as well as their acid-addition salts;

6. 5-(purin-9-yl)-5-desoxy-1.4;3.6-dianhydro-L-iditol derivatives of the general formula X

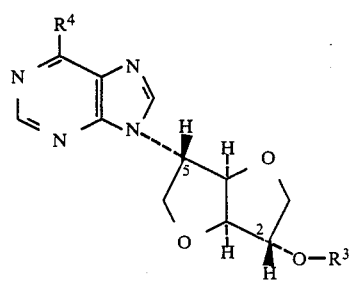
(X)

wherein $R^3$ and $R^4$ possess the meanings mentioned in claim 6, as well as their acid-addition salts;

7. 5-(purin-9-yl)-5-desoxy-1.4;3.6-dianhydro-D-glucitol derivatives of the general formula XI,

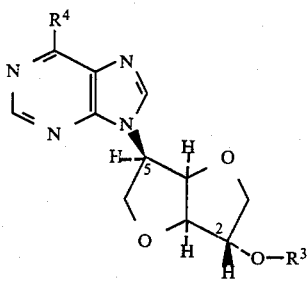

(XI)

wherein $R^3$ and $R^4$ possess the meanings mentioned in claim 6, as well as their acid-addition salts;

8. 2-(purin-9-yl)-2-desoxy-1.4;3.6-dianhydro-D-glucitol derivatives of the general formula XII

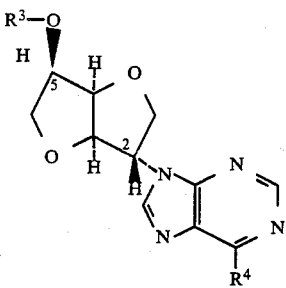

(XII)

wherein $R^3$ and $R^4$ possess the meanings mentioned in claim 6, as well as their acid-addition salts;

9. 2-(purin-9-yl)-2-desoxy-1.4;3.6-dianhydro-D-mannitol derivatives of the general formula XIII

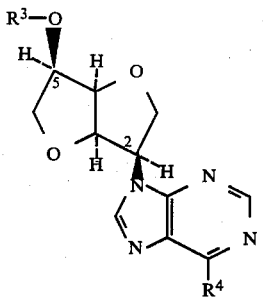

(XIII)

wherein $R^3$ and $R^4$ possess the meanings mentioned in claim 6, as well as their acid-addition salts;

10. (theophyllin-7-yl)-deoxy-1.4;3.6-dianhydrohexitol derivatives of the general formula XIV,

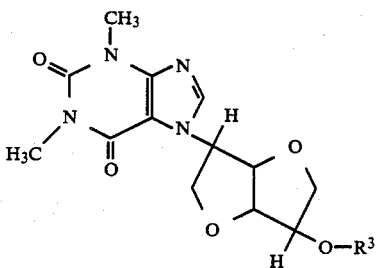

(XIV)

wherein $R^3$ signifies a hydrogen atom, a methanesulphonyl or toluenesulphonyl group, as well as their acid-addition salts;

11. (ω-purinylalkylamino)-desoxy-1.4;3.6-dianhydrohexitol derivatives of the general formula XV,

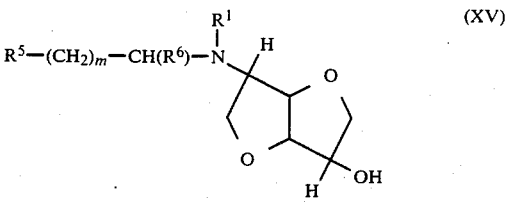

(XV)

wherein $R^1$ signifies a hydrogen atom or a lower alkyl group with 1 to 4 C-atoms, $R^5$ the adenin-9-yl radical, the theophyllin-7-yl radical, the theobromin-1-yl radical or a further N,N'-di-lower alkylxanthin-N''-yl radical, whereby "lower alkyl" signifies an alkyl group with 1 to 5 C-atoms, $R^6$ a hydrogen atom or a methyl group and m a whole number from 1 to 6, as well as their acid-addition salts;

12. ω-(theophyllin-7-yl)-alkylaminodesoxy-1.4;3.6-dianhydrohexitols of the general formula XVI,

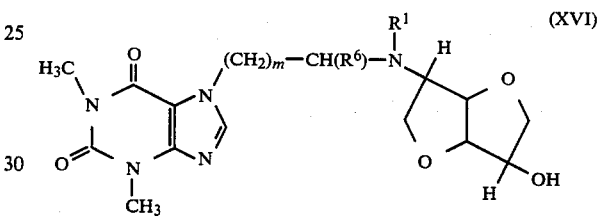

(XVI)

wherein $R^1$, $R^6$ and m possess the meanings mentioned in claim 12, as well as their acid-addition salts;

13. various processes for the preparation of the compounds according to the invention and 14. the use of the compounds according to the invention as reactive intermediate products for the preparation of the corresponding aminodesoxy-1.4;3.6-dianhydrohexitol nitrates.

As follows from the above general formulae, by "amino" derivatives there are also understood those derivatives in which the nitrogen atom is a component of an aromatic or non-aromatic heterocyclic ring system and which is possibly annelated with a further heterocyclic ring system, especially also purine derivatives, such as possibly 6-N-substituted adenine, theophylline or other dialkylxanthine derivatives.

The compounds according to the invention possess four asymmetric C-atoms in the 1.4;3.6-dianhydrohexitol basic structure and are present in optically-active form since, as starting compounds, there are used optically pure 1.4;3.6-dianhydrohexitols which are easily obtainable from naturally-occurring sugars or sugar alcohols.

The further working up of the reactive intermediate products according to the invention to give the end products, thus the corresponding mononitrates, takes place in such a manner that the free hydroxyl group of the corresponding possibly N-substituted aminodesoxy-1.4;3.6-dianhydrohexitol ($R^3$=H), which is possibly previously obtained by alkaline hydrolysis of the corresponding mesylate or tosylate ($R^3$=methanesulphonyl, toluene sulphonyl), is esterified with nitric acid, nitrating acid or with a mixture of nitric acid and glacial acetic acid/acetic anhydride, possibly in the presence of urea, to give the corresponding aminodesoxy-1.4;3.6- dianhydrohexitol nitrate. The further working up is also described in the three already mentioned simultaneously filed patent applications (cf. in particular, the Examples therein).

The compounds according to the invention can be prepared starting from the epimeric, unsubstituted 1.4;3.6-dianhydrohexitols, thus starting from L-isoidide, D-isosorbide and D-isomannide, whereby, in each case, several different synthesis routes are possible.

According to the invention, one of these routes consists in that the corresponding 1.4;3.6-dianhydrohexitol is converted with a sulphonic acid chloride, preferably with methanesulphonic acid chloride or toluenesulphonic acid chloride, in a suitable anhydrous solvent and in the presence of an adjuvant base, preferably in a pyridine or in chloroform/triethylamine, at a reduced temperature, preferably between $-20°$ and $+10°$ C., into the corresponding mono-O-acyl-1.4;3.6-dianhydrohexitol, which then, by the addition of an aqueous, for example 25%, ammonia solution or by the addition of a primary or secondary alkylamine with 1 to 4 C-atoms, by the addition of 1-aminoadamantane or by the addition of a cyclic, non-aromatic secondary amine possibly containing a further hetero atom, possibly with the addition of a suitable solvent, is subjected to an aminolysis, namely, advantageously under elevated pressure, preferably at a pressure of from 2 to 20 ats., and elevated temperature, preferably at $90°$ to $180°$ C. The aminolysis is expediently carried out in a closed steel autoclave up to quantitative reaction. Suitable solvents are—possibly with the addition of water—e.g. alcohols, di- or polyglycol ethers or dioxan.

The aminolysis of the corresponding mono-O-acyl-1,4;3.6-dianhydrohexitol can also be carried out under normal pressure but, nevertheless, at an elevated temperature, namely, when, instead of a primary or secondary amine, there is used an alkali metal salt of adenine, 6-chloro- or 6-alkylmercaptopurine or of theophylline, whereby one preferably adds dipolar aprotic solvents thereto, e.g. dimethylformamide or dimethyl sulphoxide, and preferably works at temperatures between $90°$ and $120°$ C., and stirs the reaction mixture for several days.

In the case of the aminolysis to the corresponding possibly N-mono or di-substituted aminodesoxy-1.4;3.6-dianhydrohexitol, the mesylate or tosylate group is replaced by the amino or substituted amino group or by the possibly substituted purinyl radical according to the reaction mechanism of a typical bimolecular nucleophilic substitution ($S_n2$ reaction), which always involves a reversal of configuration on the central carbon atom. This reversal of configuration, which is also known to the expert by the terms "inversion" or "Walden inversion", is the reason why, from the 1.4;3.6-dianhydro-D-glucitol 5-acyl derivative, in which the acyl radical is present in the endo-standing 5-position, there always results the 1.4;3.6-dianhydro-L-iditol derivative substituted in the 5-position by the amino group or the possibly substituted amino group or the possibly substituted purinyl radical, in which the substituent entering into the molecule in place of the acyl radical no longer stands in the endo- but rather in the exo-position. The Walden inversion involved with the $S_N2$ reaction is, in completely corresponding manner, responsible for the fact that, from the corresponding iditol acylate, there always results the glucitol derivative endo-substituted in the 5-position, from the mannitol acylate the corresponding glucitol derivative exo-substituted in the 2-position and from the glucitol-2-exo-acylate, the corresponding mannitol derivative endo-substituted in the 2-position.

For the preparation of those compounds of general formula I according to the invention wherein $R^1$ and $R^2$, together with the nitrogen atom to which they are bound, signify an aden(9)yl radical mono- or disubstituted on the 6-amino group, there is first prepared, as described above, the corresponding 6-chloropurin-9-yl or 6-alkylmercaptopurin-9-yldesoxy-1.4;3.6-dianhydrohexitol, namely, by reaction of the 6-chloropurine or 6-alkylmercaptopurine-9-sodium salt with the corresponding monoacyldesoxy-1.4;3.6-dianhydrohexitol. The 6-chloropurin-9-yl- or 6-alkylmercaptopurin-9-yldesoxy-1.4;3.6-dianhydrohexitol is then reacted at a temperature between $90°$ and $150°$ C. in a closed autoclave with an aqueous alkylamine or dialkylamine solution, whereby the alkyl group has 1 to 4 C-atoms, with a cyclic, nonaromatic secondary amine possibly containing a further hetero atom or with a possibly halogen-substituted ω-phenylalkylamine, the alkyl group of which has 1 to 8 C-atoms, whereby water or a lower alcohol is possibly added thereto as solvent.

Examples of the primary and secondary amines used for this purpose are: methylamine, ethylamine, propylamine, isopropylamine, butylamine, dimethylamine, diethylamine, dipropylamine, dibutylamine, pyrrolidine, piperidine, morpholine, methylpiperazine, benzylamine, 2-phenylethylamine, 3-phenylpropylamine, 4-phenylbutylamine, 5-phenylpentylamine, 6-phenylhexylamine, 7-phenylheptylamine, 8-phenyloctylamine, as well as the corresponding ω-phenylalkylamines ortho-, meta- or para-halogen-substituted in the phenyl ring.

For the preparation of those compounds according to the invention in which the nitrogen atom of the aminodesoxy-isohexide ring system is connected by a straight-chained, unsubstituted alkyl group with one of the ring nitrogen atoms of a purine derivative, thus of an adenine, xanthine, theophylline or theobromine derivative, the corresponding aminodesoxy-1.4;3.6-dianhydrohexitol is preferably reacted with an N-(ω-bromo-, ω-chloro- or ω-methanesulphonyloxyalkyl)-theophylline, -theobromine, -dialkylxanthine or -adenine, preferably with 7-(2-bromoethyl)-theophylline, 7-(3-chloropropyl)-theophylline, 7-(3-bromopropyl)-theophylline, 7-(3-methanesulphonyloxypropyl)-theophylline, 7-(4-bromobutyl)-theophylline, 7-(5-bromopentyl)-theophylline, 7-(6-bromohexyl)-theophylline and the like.

For the avoidance of a disubstitution on the nitrogen atom of the amino group of the aminoisohexide, this amino group can, before the reaction with the reactive purine derivative, be reacted with a compound suitable as a protective group, for example a benzyl compound, which, after the reaction, can easily be split off again, for example, by hydrogenation in the presence of a conventional noble metal catalyst.

A further suitable process of the preparation of those compounds according to the invention in which the "bridge" between the aminoisohexide and the purine derivative is an alkylene group consists in that one subjects the corresponding aminoisohexide, together with an ω-acylalkyl- or ω-oxoalkylxanthine or -adenine derivative, in per se known manner to a reductive condensation in the presence of hydrogen and of a suitable noble metal or noble metal sulphide catalyst, possibly in the presence of a solvent. In the case of the ω-oxoalkylxanthine or -adenine derivatives, for example of 7-(3-oxopropyl)-theophylline, there results the corresponding purinylalkylaminoisohexide derivatives with unbranched alkylene bridge, for example 3-theophyllin-7-ylpropylaminoisohexide. In the case of the ω-acylalkylxanthine or -adenine derivatives, e.g. of 7-(2-acetylethyl)-theophylline or of 7-(4-acetylbutyl)-theophylline, there results, in the case of the reductive condensation with the aminoisohexide, the corresponding ω-purinylalkylaminoisohexide derivatives with branched alkylene group, for example 3-theophyllin-7-yl-1-methylpropylaminoisohexide or 5-theophyllin-7-yl-1-methylpentylaminoisohexide. The so obtained compounds according to the invention with branched alkylene bridge possess an additional centre of asymmetry so that, in each case, two diastereomers result in the case of the reductive condensation, which, with the help of conventional methods of separation, for example by column chromatography, liquid-liquid partitioning or fractional crystallisation, can be separated into the two isomers, thus, for example into (+)-5-(3-theophyllin-7-yl-1-methylpropylamino)-5-desoxy-1.4;3.6-dianhydro-L-iditol and (−)-5-(3-theophyllin-7-yl-1-methylpropylamino)-5-desoxy-1.4;3.6-dianhydro-L-iditol. The separation can also first take place after the further working up to the nitric acid esters.

The hitherto described first route according to the invention for the preparation of the compounds according to the invention, in which the corresponding isohexide is converted with a sulphonic acid chloride, preferably with methanesulphonic acid chloride or toluenesulphonic acid chloride, into the corresponding monoacyl-1.4;3.6-dianhydrohexitol, has the disadvantage that, in the case of the acylation, there results not only the corresponding 5-O-acyl derivative or 2-O-acyl derivative but, at the same time, also the 2,5-diacyl derivative so that, in the case of the isoidide and isomannide derivative, in each case the monoacyl compound must be separated from the diacylate, whereas in the case of the isosorbide, in which two stereoisomeric monoacyl derivatives result, besides the diacylate, the desired acylate must be isolated from the mixture of the three acyl derivatives. The separation of the acylate mixture takes place either by fractional crystallisation, fractional extraction or with the help of other per se known methods.

However, the laborious and time-consuming separation of the acylate mixture is avoided in the case of the use of a further synthesis route according to the invention in that 1.4;3.6-dianhydro-D-glucitol is reacted quantitatively with an excess of sulphonic acid chloride, preferably methanesulphonyl chloride or toluenesulphonyl chloride, in pyridine or chloroform/triethylamine to give the corresponding 1.4;3.6-dianhydro-D-glucitol-2,5-diacylate.

The diacylate is then subjected to the aminolysis under conditions corresponding to those described in the first synthesis route, whereby, as a result of preferred substitution of the 5-endo-acyl group with reversal of configuration and as a result of partial hydrolysis of the 2-exo-acyl group, with maintenance of the configuration, besides a small amount of 2,5-diamino-2,5-didesoxy-1.4;3.6-dianhydro-D-glucitol remaining in the aqueous phase, there results a mixture of 5-amino-5-desoxy-1.4;3.6-dianhydro-L-iditol and 5-amino-5-desoxy-1.4;3.6-dianhydro-L-iditol 2-methanesulphonate in a ratio of about 1:4.

For the completion of the hydrolysis of the 2-exoacyl group, this 1:4 mixture is then subjected to an alkaline or acidic hydrolysis and the resulting 5-amino-5-desoxy-1.4;3.6-dianhydro-L-iditol is subsequently possibly condensed with the desired reactive purinylalkyl derivative.

As follows from the fact that the aminolysis of the isosorbide 2,5-diacylate preponderantly leads to the 5-aminoisoidide 2-acylate, the nucleophilic substitution of the 2-exo-acylate group in the isosorbide diacylate is sterically hindered. The degree of steric hindrance is temperature-dependent. In order to obtain the 5-aminoisoidide 2-acylate as quantitatively as possible from the corresponding diacylate, one works, therefore, according to the invention, preferably at a temperature of 80° to 110° C. since, at temperatures above 110° C., the 2-exo-acyl group is also attacked, even though to a small extent, by ammonia or by the amine used. An alcohol, preferably ethanol, can be added as solubiliser to the aqueous ammonia solution or to the amine. In the case of the aminolysis by purine alkali metal salts, one uses dipolar aprotic solvents, preferably dimethyl sulphoxide, dimethylformamide or diethers of mono-, di- or polyethylene glycols.

In the case of a further route according to the invention for the preparation of the compounds according to the invention, one makes use of the surprisingly found fact that 1.4;3.6-dianhydro-D-glucitol 2,5-diacylates (dimesylate or ditosylate) are selectively attacked on the $C^5$-atom by sodium benzoate or other alkali metal salts of benzoic acid in a suitable solvent, preferably a dipolar aprotic solvent, for example in anhydrous dimethylformamide, dimethyl sulphoxide or diethers of ethylene glycol, at temperatures of 100° to 180°, preferably of 120° to 150° C., so that, with reversal of configuration, 1.4;3.6-dianhydro-L-iditol 2-methanesulphonate 5-benzoate or 1.4;3.6-dianhydro-L-iditol 2-toluenesulphonate 5-benzoate result in high yield. This product is now again subjected to the ammonolysis with 25% ammonia solution or to the aminolysis under elevated pressure and elevated temperature, whereby the benzoic acid ester is split off not with substitution but rather hydrolytically, namely, with maintenance of the configuration on the $C^5$-atom, whereas the acylate residue on the $C^2$-atom, with reversal of configuration, is substituted by the amino or alkylamino group to give the corresponding 5-amino-5-desoxy-1.4;3.6-dianhydro-D-glucitol or 5-alkylamino-5-desoxy-1.4;3.6-dianhydro-D-glucitol.

Since the last-mentioned elegant process involves a double selective reversal of configuration, the configuration of the end product is, with regard to its substituents, identical with the configuration of the starting compound; from the isosorbide disulphonate there again results an isosorbide derivative, namely 5-amino- or 5-alkylamino-5-desoxy-1.4;3.6-dianhydro-D-glucitol.

The so obtained 5-amino- or 5-alkylamino-5-desoxy-1.4;3.6-dianhydro-D-glucitol derivatives can subsequently be condensed by the previously described reaction routes with reactive purinylalkyl derivatives to give the 5-(ω-purinylalkylamino)-5-desoxy-1.4;3.6-dianhydro-D-glucitol derivatives according to the invention.

Instead of the free bases, there can possibly also be used the acid-addition salts of the compounds according to the invention, namely, the addition salts of inorganic acids and mineral acids, for example of the hydrohalic acids, sulphuric acid or phosphoric acids, as well as of organic acids, for example of the carboxylic and sulphonic acids. The free bases can again be liberated from the acid-addition salts by treatment with strong bases, for example sodium or potassium hydroxide.

The abbreviations used in the following Examples have the following meanings:

m.p. = melting point (uncorrected)
(decomp.) = decomposition
d = density
$[\alpha]_D^{25}$ = optical rotation at 25° C., sodium D-line.

After the optical rotational values are given the concentrations of the measured solutions, whereby, for example c 2 means a concentration of 2 g./100 ml. of solution: the solvent is, in each case, stated separately. All temperatures are given in degrees Celsius.

EXAMPLE NO. 1

5-Amino-5-desoxy-1.4;3.6-dianhydro-iditol (a) 1.4;3.6-Dianhydro-D-glucitol 2-methanesulphonate, 5-methanesulphonate and 2.5-dimethanesulphonate:

To a solution of 4.82 kg. (33 mol) 1.4;3.6-dianhydro-D-glucitol in 24 liters pyridine, one adds dropwise, with the exclusion of moisture, stirring and cooling to $-15°$ to $-20°$, within the course of several hours, 3.1 liters (40 mol) methanesulphonic acid chloride. Subsequently, one further stirs for 15 hours without cooling. One distils off the pyridine in vacuo, adds 15 liters of water to the oily residue, boils up and allows to cool. Suction filtration, washing with 4 liters of water and drying of the crystalline precipitate gives 2.22 kg. (7.34 mol) 1.4;3.6-dianhydro-D-glucitol 2,5-dimethanesulphonate. The filtrate is neutralised, with stirring and water cooling, with about 1.5 kg. sodium hydroxide and evaporated to dryness at about 70° in a vacuum. The dry residue is continuously hot extracted with a total of 30 liters of chloroform and the extract filtered hot. One allows the extract to stand for 15 hours at 20°, filters off the crystalline precipitate with suction, washes it twice with 2 liter amounts of chloroform, dries and obtains 2.3 kg. (10.26 mol) 1.4;3.6-dianhydro-D-glucitol 5-methanesulphonate. The combined filtrates are evaporated in a vacuum and the residue dissolved hot in 22 liters ethanol. One leaves to stand for 15 hours at 20°, filters off the crystalline precipitate with suction, washes it twice with 3 liter amounts of ethanol, dries and obtains 0.65 kg. (2.90 mol) 1.4;3.6-dianhydro-D-glucitol 2-methanesulphonate. Evaporation of the filtrate gives 2.21 kg. (9.85 mol) of a mixture of the two isomeric monomethanesulphonates which, according to need, can be further separated by repetition of the alternating crystallisations from chloroform and ethanol or, by esterification with methanesulphonic acid chloride in pyridine, completely converted into 1.4;3.6-dianhydro-D-glucitol 2,5-dimethanesulphonate.

Analytical amounts of the methanesulphonates give, after recrystallisation, correct elementary analyses and the melting points and optical rotations set out in Table 1:

TABLE 1

| 1.4;3.6-dianhydro-D-glucitol | recrystallised from | m.p. [°C.] | $[\alpha]_D^{25}$ |
|---|---|---|---|
| 2-methane-sulphonate | chloroform | 135–138.5 | 62.5 (c 2; acetone) |
| 5-methane sulphonate | chloroform | 123–124 | 75.9 (c 2; methanol) |
| 2,5-dimethane-sulphonate | ethanol/acetone | 127–128 | 74 (c 2; acetone) |

Remark:
If one reacts 1.4;3.6-dianhydro-D-glucitol with the 2 to 2.5 fold molar amount of methanesulphonic acid chloride under the same reaction conditions, one obtains 1.4;3.6-dianhydro-D-glucitol 2,5-dimethanesulphonate in almost quantitative yield.

(b) 5-Amino-5-desoxy-1.4;3.6-dianhydro-L-iditol:

The product can be obtained in the following 2 ways:

Process 1:

Preparation by ammonolysis of 1.4;3.6-dianhydro-D-glucitol 5-methanesulphonate. A mixture of 448 g. (2 mol) 1.4;3.6-dianhydro-D-glucitol 5-methanesulphonate and 1.5 liters of 25% aqueous ammonia (20 mol) is stirred in a closed steel autoclave for 24 hours at 130°. Thereafter, the reaction is quantitative. One evaporates under reduced pressure and azeotropically dries by the successive addition and renewed evaporation of 1 liter amounts of ethanol and chloroform. The oily residue is dissolved, with warming, in 500 ml. ethanol and diluted to 2 liters with isopropanol. Upon cooling, 311 g. (1.3 mol) 5-amino-5-desoxy-1.4;3.6-dianhydro-L-iditol crystallise out as methanesulphonic acid salt. A further 100 g. (0.4 mol) of crystalline pure product are obtained by treatment of the mother liquor with 30 g. active charcoal and concentration of the filtrate. For analysis, one recrystallises from ethanol/chloroform.

M.p. 151°–4°; $[\alpha]_D^{25}$ 27.6 (c 1; water).

Elementary analysis: $C_6H_{11}NO_3 \times CH_3SO_3H$ (241.27); calc.: C (34.83); H (6.27), N (5.81); found: C (34.71), H (6.45), N (5.36).

A small amount of the product is converted into the free base and recrystallised from chloroform/ether.

M.p. 103°–104°; $[\alpha]_D^{25}$ 31.6 (c 2; water).

Process 2:

Ammonolysis of 1.4;3.6-dianhydro-D-glucitol 2,5-dimethanesulphonate, followed by alkaline hydrolysis of the 5-amino-5-desoxy-1.4;3.6-dianhydro-L-iditol 2-methanesulphonate obtained.

A mixture of 302 g. (1 mol) 1.4;3.6-dianhydro-D-glucitol 2,5-dimethanesulphonate, 750 ml. 25% aqueous ammonia (10 mol) and 750 ml. ethanol is stirred for 4 days at 100° in a closed steel autoclave. After cooling, one mixes with 1 liter of water and filters off with suction from unreacted dimethanesulphonate which has crystallised out (106 g. = 0.35 mol). For the removal of ammonia, the filtrate is mixed with 104 g. (1.3 mol) sodium hydrogen carbonate and evaporated under reduced pressure. One dissolves in 5 liters of water and extracts elimination products therefrom with 500 ml. chloroform. The aqueous phase is continuously extracted with chloroform for 48 hrs. in a rotary perforator (Normag). 2,5-Diamino-2,5-didesoxy-1.4;3.6-dianhydro-D-glucitol formed as by-product remains in the aqueous phase. The chloroform extract gives, after drying over anhydrous sodium sulphate, filtering and evaporating, 105 g. (about 0.55 mol) of a 1:4 mixture of 5-amino-5-desoxy-1.4;3.6-dianhydro-L-iditol and 5-amino-5-desoxy-1.4;3.6-dianhydro-L-iditol 2-methanesulphonate.

For the characterisation of the latter product, a small portion of the mixture is dissolved in chloroform, washed 2 times with water, the chloroform phase evaporated, converted into the methanesulphonic acid salt and recrystallised twice from ethanol.

M.p. 213°–5°; $[\alpha]_D^{25}$ 39.0 (c 0.50; water).

Elementary analysis: $C_7H_{13}NO_5S \times CH_3SO_3H$ (319.37); calc.: C (30.09), H (5.37), N (4.39), S (20.08); found: C (30.13), H (5.49), N (4.25), S (20.6).

The above-obtained mixture is added to a solution of 60 g. (1.5 mol) sodium hydroxide in 1.5 liters of water and boiled under reflux for 24 hours. After cooling, one adjusts to pH=10 by the addition of conc. hydrochloric acid, filters and evaporates under reduced pressure, dries azeotropically with n-butanol, heats the residue with 500 ml. n-butanol, heats the residue with 500 ml. n-butanol and filters off from inorganic salts. The butanolic solution is evaporated, the residue is dissolved in 200 ml. isopropanol and mixed with 34 g. (0.35 mol) methanesulphonic acid. 80 g. (0.33 mol) 5-Amino-5-desoxy-1.4;3.6-dianhydro-L-iditol crystallise out in the form of the methanesulphonic acid salt. M.p. 150°-2°. Yield, referred to reacted 1.4;3.6-dianhydro-D-glucitol 2,5-dimethanesulphonate: 50%.

EXAMPLE NO. 2

5-Amino-5-desoxy-1.4;3.6-dianhydro-L-iditol

To a solution of 2923 g. (20 mol) 1.4:3.6-dianhydro-D-glucitol in 16 liters of anhydrous pyridine, one adds dropwise, with stirring and cooling to −15°, 2 liters (25 mol) methanesulphonic acid chloride, stirs for 15 hrs. at −15° and distils off the pyridine under reduced pressure. The oily residue is mixed with 10 liters of water, briefly heated to boiling and, after cooling, filtered off from 1.4;3.6-dianhydro-D-glucitol 2,5-dimethanesulphonate which has crystallised out and the filter cake is washed 2 times with 2.5 liters amounts of water. The combined filtrates are, after the addition of 1 kg. (25 mol) sodium hydroxide, evaporated under reduced pressure. The residue, consisting of a mixture of 1.4;3.6-dianhydro-D-glucitol 2- and 5-methanesulphonate and sodium methanesulphonate, is, without further purification, subjected to aqueous ammonolysis. For this purpose, one mixes with 4 liters of water and 12 liters of 25% aqueous ammonia and heats the solution thus obtained for 2 days, with stirring, in a closed steel autoclave to 120° (pressure: about 7-8 bar). After cooling and decompressing, one adds 400 g. active charcoal thereto, filters, concentrates the filtrate to about 4 liters and extracts therefrom twice with 1 liter amounts of chloroform the 1.4;2.5;3.6-trianhydro-D-mannitol formed as by-product (in all about 90 g.=0.7 mol) from the 1.4;3.6-dianhydro-D-glucitol 2-methanesulphonate. The aqueous phase is brought to pH=9 by the addition of sodium hydroxide and evaporated to dryness. The semi-solid residue is, for the separating off of inorganic material, boiled with 10 liters of ethanol and, after cooling, filtered. The evaporated filtrate is dissolved, with warming, in 10 liters of n-butanol, dried over anhydrous sodium sulphate, filtered, evaporated and fractionally distilled in vacuo. After a pre-running (0.4 mm.Hg 122°-135°) of 55 g. (0.38 mol) 5-amino-5-desoxy-1.4;3.6-dianhydro-L-iditol slightly contaminated with trianhydro-D-mannitol, there distil, between 140° and 144° at 0.15 to 0.2 mm.Hg, a total of 681 g. (4.69 mol) pure 5-amino-5-desoxy-1.4;3.6-dianhydro-L-iditol as a slowly solidifying pale yellowish oil. M.p. (after recrystallisation from chloroform/ethyl acetate/ether) 103°-4°; $[\alpha]_D^{25}$ 31.6 (c 2.0; water).

EXAMPLE NO. 3

5-Amino-5-desoxy-1.4;3.6-dianhydro-D-glucitol

The product can be obtained in the following two ways:

Process I:

Preparation and ammonolysis of 1.4;3.6-dianhydro-L-iditol 2-methanesulphonate.

A solution of 73 g. (480 mmol) 96% 1.4;3.6-dianhydro-L-iditol in 500 ml. anhydrous pyridine is mixed dropwise, with the exclusion of moisture, stirring and cooling to −20°, with 52 ml. (660 mmol) 98% methanesulphonyl chloride and then stirred for 15 hours at −20°. The pyridine is distilled off as far as possible under reduced pressure and the residue, after the addition of 500 ml. hot water, heated until it dissolves. Upon cooling, 47.6 g. (157 mmol) 1.4;3.6-dianhydro-L-iditol 2,5-dimethanesulphonate crystallise out, which are filtered off with suction and then washed twice with 100 ml. amounts of water. The combined filtrates are neutralised (pH=7) by the addition of sodium hydrogen carbonate, evaporated under reduced pressure and dried. The powdered dry residue is boiled out twice with 400 ml. amounts of chloroform and filtered while still hot. After cooling the filtrate, 1.4;3.6-dianhydro-L-iditol 2-methanesulphonate crystallises out. The mother liquor provides further monomethanesulphonate after concentration. In all, one obtains 51.5 g. (213 mmol) 1.4;3.6-dianhydro-L-iditol 2-methanesulphonate. For analysis, a small amount is recrystallised from methanol. M.p. 124°-5°; $[\alpha]_D^{25}$ 33.7 (c 1.0; acetone).

Elementary analysis: $C_7H_{12}O_6S$ (224.24); calc.: C (37.50), H (5.40), S (14.30); found: C (37.58), H (5.53), S (14.0).

33.6 g. (150 mmol) of the so obtained 1.4;3.6-dianhydro-L-iditol 2-methanesulphonate, together with a solution of 17 g. (1 mol) ammonia, are heated in 250 ml. n-butanol in a closed steel autoclave for 3 days at 170°. After cooling, one filters off with suction the ammonium methanesulphonate which has crystallised out and washes with 100 ml. n-butanol. The filtrate is extracted twice with 100 ml. amounts of water. The combined aqueous extracts are washed with 200 ml. chloroform, evaporated to dryness and dried azeotropically with butanol. The dry residue is boiled with 50 ml. n-butanol, with the addition of 10 g. anhydrous sodium sulphate, filtered hot and the filtrate evaporated. The oily crude product thus obtained is taken up in 50 ml. chloroform, filtered and evaporated. One obtains 14 g. (96 mmol) of slowly solidifying 5-amino-5-desoxy-1.4;3.6-dianhydro-D-glucitol. For characterisation, one converts a small portion of the product into the hydrochloride and recrystallises from isopropanol.

Decomposition point: 240°; $[\alpha]_D^{25}$ 39.1 (c 1.0; water).

Elementary analysis: $C_6H_{11}NO_3 \times HCl$ (181.63); calc.: C (39.68), H (6.66), N (7.71), Cl (19.52); found: C (39.85), H (6.89), N (7.66), Cl (19.3).

Process II:

Preparation and selective ammonolysis of 1.4;3.6-dianhydro-L-iditol 2-methanesulphonate 5-benzoate.

A mixture of 604 g. (2 mol) 1.4;3.6-dianhydro-D-glucitol 2,5-dimethanesulphonate, 317 g. (2.2 mol) sodium benzoate and 8 liters of anhydrous dimethylformamide is stirred for 2 days at 145° in a steel autoclave under a protective atmosphere of nitrogen. The dimethylformamide is distilled off under reduced pressure, the residue is taken up in 5 liters of chloroform, successively extracted with 2 liter amounts of 1 molar aqueous sodium hydroxide solution and water, the chloroform phase is dried over anhydrous sodium sulphate and concentrated to a volume of 1500 ml. The crude product which crystallises out upon standing is filtered off with suction, dissolved in 500 ml. acetone with warming and the hot solution poured into 1000 ml. ethanol. Upon cooling, 273 g. (0.83 mol) 1.4;3.6-dianhydro-L-iditol 2-methanesulphonate 5-benzoate crystallise out. After evaporating and recrystallisation, the mother liquor gives a further 120 g. (0.37 mol) of product slightly contaminated with starting substance. The analytical sample has, after recrystallisation from ethanol, the m.p. of 117° and $[\alpha]_D^{25}$ 76.6 (c 2; chloroform).

Elementary analysis: $C_{14}H_{16}O_7S$ (328.35); calc.: C (51.21), H (4.91), S (9.76); found: C (51.60), H (5.05), S (9.6).

328 g. (1 mol) of the so obtained 1.4;3.6-dianhydro-L-iditol 2-methanesulphonate 5-benzoate, together with 1 liter ethanol and 1.5 liter of 25% aqueous ammonia, are stirred for 1 day at 130° in a closed steel autoclave. One evaporates under reduced pressure, dissolves the residue in 1 liter of water, adjusts to pH=1 by the addition of conc. hydrochloric acid and filters off the precipitate—consisting of benzoic acid and benzamide—with suction. The filtrate is, after washing twice with 500 ml. amounts of chloroform, adjusted to pH=8 by the addition of sodium hydrogen carbonate, again evaporated and the residue extracted with 2 liters of ethanol. The ethanol extract is, after evaporation, extracted with 2 liters of chloroform, the chloroform extract boiled up with 60 g. active charcoal, filtered and evaporated. The so obtained 105 g. of crude product give, after fractional distillation at 0.2 mm.Hg and 136°–142° distilling over temperature, 86.3 g. (0.59 mol) 5-amino-5-desoxy-1.4;3.6-dianhydro-D-glucitol in the form of a slowly solidifying, colourless oil which, after conversion into the hydrochloride, is identical to the product obtained according to Process I.

EXAMPLE NO. 4

2-Amino-2-desoxy-1.4;3.6-dianhydro-D-glucitol (a) 1.4;3.6-Dianhydro-D-mannitol 2-methanesulphonate To a solution of 877 g. (6 mol) 1.4;3.6-dianhydro-D-mannitol in 6 liters of pyridine one adds dropwise, with stirring and exclusion of moisture, as well as cooling to −15°, within 6 hrs., 525 ml. (6.6 mol) methanesulphonyl chloride, stirs for a further 3 days at −15° and then distils off the pyridine under reduced pressure. Upon mixing the oily residue with 2.7 liters of water, pure 1.4;3.6-dianhydro-D-mannitol 2,5-dimethanesulphonate crystallises out, which is separated off and washed 2 times with 700 ml. of water. The combined filtrates are mixed with a solution of 264 g. (6.6 mol) sodium hydroxide in 2.5 liters of water, adjusted to pH=7 by the addition of sodium hydrogen carbonate, evaporated under reduced pressure and dried azeotropically with chloroform. The residue is hot extracted twice with 2.5 liter amounts of chloroform and filtered. The combined chloroform extracts are extracted 5 times with 1 liter amounts of water. Upon concentration of the aqueous phases, 1.4;3.6-dianhydro-D-mannitol 2-methanesulphonate crystallises out. The mother liquor remaining after the suction filtration gives, after evaporation and recrystallisation from ethanol, further product. Residual product is obtained by evaporation of the ethanolic mother liquor, dissolving of the residue in water and continuous extraction of the aqueous solution with chloroform in a rotary perforator. Unreacted 1.4;3.6-dianhydro-D-mannitol remains in the aqueous phase. In all, one obtains 396 g. (1.77 mol) 1.4;3.6-dianhydro-D-mannitol 2-methanesulphonate (besides 465 g. = 1.54 mol of the dimethanesulphonate). The analytical sample has, after recrystallisation from chloroform, the m.p. 111°–112° and $[\alpha]_D^{25}$ 118 (c 1.0; acetone).

Elementary analysis: $C_7H_{12}O_6S$ (224.24); calc.: C (37.50), H (5.40), S (14.30); found: C (37.41), H (5.59), S (13.7).

(b) 2-Amino-2-desoxy-1.4;3.6-dianhydro-D-glucitol:

A mixture of 224 g. (1 mol) of the previously obtained 1.4;3.6-dianhydro-D-mannitol 2-methanesulphonate and 1 liter of 25% aqueous ammonia is stirred for 24 hrs. at 120° in a closed steel autoclave. After cooling, one adds 84 g. (1 mol) sodium hydrogen carbonate thereto, evaporates under reduced pressure and boils out the residue with 2 liters n-butanol. The evaporated butanol extract is taken up in 1 liter of chloroform, residual sodium methanesulphonate is filtered off and the filtrate evaporated. One obtains 130 g. (0.9 mol) 2-amino-2-desoxy-1.4;3.6-dianhydro-D-glucitol as a pale yellowish oil. For characterisation, one converts a small portion into the hydrochloride and recrystallises from isopropanol/methanol/chloroform.

M.p. 230° (decomp.); $[\alpha]_D^{25}$ 52.1 (c 1.0; water).

Elementary analysis: $C_6H_{11}NO_3 \cdot xHCl$ (181.62); calc.: C (39.68), H (6.66), N (7.71), Cl (19.52); found: C (39.59), H (6.89), N (7.52), Cl (19.3).

EXAMPLE NO. 5

2-Amino-2-desoxy-1.4;3.6-dianhydro-D-mannitol

A mixture of 448 g. (2 mol) 1.4;3.6-dianhydro-D-glucitol 2-methanesulphonate (preparation see Example 1(a) and 1500 ml. of 25% aqueous ammonia is stirred for 1 day at 130° in a closed steel autoclave. After cooling, one adds 30 g. active charcoal thereto, filters and extracts with 1 liter of chloroform the 1.4;2.5;3.6-trianhydro-D-mannitol formed as by-product [after evaporation of the chloroform phase and recrystallisation from ether/petroleum ether, in all 104 g. (0.81 mol)]. The aqueous phase is, after evaporation under reduced pressure and azeotropic drying with ethanol and chloroform, extracted at boiling temperature with 2 liters of isopropanol. Upon concentration of the isopropanol extract to 0.5 liter, ammonium methanesulphonate which has crystallised out is filtered off, the filtrate is neutralised with dilute aqueous sodium hydroxide solution, evaporated and extracted hot with 1 liter n-butanol. The butanol extract is evaporated and the residue extracted with 1 liter of chloroform. Evaporation of the filtered chloroform extract gives 60 g. (0.41 mol) of oily crude base which is dissolved in 100 ml. acetic acid and mixed dropwise with a solution of 15 ml. 96% nitric acid (d = 1.5) in 75 ml. acetic acid. The hydrogen nitrate which crystallises out is filtered off with suction and recrystallised from isopropanol/ethanol. One obtains 32 g. (154 mmol) 2-amino-2-desoxy-1.4;3.6-dianhydro-D-mannitol hydrogen nitrate.

M.p. 192°–3° (decomp.): $[\alpha]_D^{25}$ 63.4 (c 0.51; water).

Elementary analysis: $C_6H_{11}NO_3 \cdot xHNO_3$ (208.18); calc.: C (34.62), H (5.81), N (13.45); found: C (34.52), H (5.97), N (13.53).

A small portion is converted into the hydrochloride and recrystallised from ethanol.

M.p. 263°–8° (decomp.): $[\alpha]_D^{25}$ 77.8 (c 1; water).

Elementary analysis: $C_6H_{11}NO_3 \times HCl$ (181.63); calc.: C (39.68), H (6.66), N (7.71), Cl (19.52); found: C (39.82), H (6.68), N (7.59), Cl (19.4).

EXAMPLE NO. 6

5-Methylamino-5-desoxy-1.4;3.6-dianhydro-L-iditol

A mixture of 22.4 g. (0.1 mol) 1.4;3.6-dianhydro-D-glucitol 5-methanesulphonate (preparation see Example 1a), 31 g. (1 mol) methylamine and 150 ml. n-butanol is stirred in a closed steel autoclave for 15 hrs. at 150° under an atmosphere of nitrogen. After cooling, one adds thereto a solution of 4 g. (0.1 mol) sodium hydroxide in 200 ml. n-butanol, stirs up, precipitates out the sodium methanesulphonate formed with 600 ml. chloroform, filters and evaporates the filtrate under reduced pressure. The so obtained oily crude base is dissolved in 100 ml. isopropanol and converted into the hydrogen nitrate with 6.5 ml. of 65% nitric acid. After evaporation under reduced pressure, one recrystallises from isopropanol and obtains 15.3 g. (68.9 mmol) 5-methylamino-5-desoxy-1.4;3.6-dianhydro-L-iditol hydrogen nitrate.

M.p. 108°–9°; $[\alpha]_D^{25}$ 41.8 (c 1.0; water).

Elementary analysis: $C_7H_{13}NO_3 \times HNO_3$ (222.20); calc.: C (37.84), H (6.35), N (12.61); found: C (38.00), H (6.60), N (12.23).

EXAMPLE NO. 7

5-Ethylamino-5-desoxy-1.4;3.6-dianhydro-L-iditol

A mixture of 11.2 g. (50 mmol) 1.4;3.6-dianhydro-D-glucitol 5-methanesulphonate, 40.5 g. (500 mmol) ethylamine hydrochloride, 20 g. (500 mmol) sodium hydroxide and 200 ml. water is stirred in a closed steel autoclave for 15 hrs. at 150° under an atmosphere of nitrogen. After cooling and decompressing, one adds thereto 2 g. (50 mmol) sodium hydroxide, evaporates to dryness under reduced pressure, extracts the residue hot with chloroform and evaporates the extract to dryness. One obtains 9 g. (about 50 mmol) of oily 5-ethylamino-5-desoxy-1.4;3.6-dianhydro-L-iditol, which is used for the subsequent esterification with nitric acid. For characterisation, a small portion is converted into the hydrochloride and recrystallised 2 times from isopropanol.

M.p. 181°–3° (decomp.): $[\alpha]_D^{25}$ 51.3 (c 1; water).

Elementary analysis: $C_8H_{15}NO_3 \times HCl$ (209.68); calc.: C (45.83), H (7.69), N (6.68), Cl (16.91); found: C (46.26), H (8.06), N (6.69), Cl (16.9).

EXAMPLE NO. 8

5-Adamant-1-ylamino-5-desoxy-1.4;3.6-dianhydro-L-iditol

A mixture of 11.2 g. (50 mmol) 1.4;3.6-dianhydro-D-glucitol 5-methanesulphonate, 39 g. (250 mmol) 1-amino-adamantane and 100 ml. n-butanol is heated for 3 days in a closed steel autoclave to 150°. Subsequently, one evaporates to dryness under reduced pressure, dissolves the residue in 250 ml. chloroform, obtains, by extraction with 1 molar hydrochloric acid, first excess adamantylamine and, in the case of further extraction, the reaction product. The hydrochloric acid solution of the reaction product is adjusted to pH=8 with dilute aqueous sodium hydroxide solution and re-extracted with chloroform. Evaporation of the chloroform phases, dried over anhydrous sodium sulphate, gives 3.85 g. (13.8 mmol) 5-adamant-1-ylamino-5-desoxy-1.4;3.6-dianhydro-L-iditol. For analysis, one recrystallises from cyclohexane.

M.p. 126°–7°; $[\alpha]_D^{25}$ 26.0 (c 1; ethanol).

Elementary analysis: $C_{16}H_{25}NO_3$ (279.39); calc.: C (68.79), H (9.02), N (5.01); found: C (68.80), H (9.25), N (5.07).

EXAMPLE NO. 9

5-Dimethylamino-5-desoxy-1.4;3.6-dianhydro-L-iditol 22.5 g. (0.5 mol) dimethylamine are dissolved, with cooling, in 100 ml. n-butanol, mixed with 11.2 g. (50 mmol) 1.4;3.6-dianhydro-D-glucitol 5-methanesulphonate and heated for 15 hrs. in a closed steel autoclave to 150°. After cooling and decompressing, one adds 100 ml. 0.5 molar butanolic sodium hydroxide solution thereto, filters and evaporates under reduced pressure. The residue is extracted with chloroform and the chloroform extract evaporated under reduced pressure. One obtains 8.5 g. (49 mmol) of oily 5-dimethylamino-5-desoxy-1.4;3.6-dianhydro-L-iditol. For characterisation, one converts a small portion into the hydrochloride and recrystallises from isopropanol.

M.p. 227°–9°; $[\alpha]_D^{25}$ 46.8 (c 0.58; water).

Elementary analysis: $C_8H_{15}NO_3 \times HCl$ (209.68); calc.: C (45.82), H (7.69), N (6.68), Cl (16.91); found: C (46.02), H (7.96), N (6.79), Cl (16.6);

EXAMPLE NO. 10

5-Diethylamino-5-desoxy-1.4;3.6-dianhydro-L-iditol

Preparation analogously to Example 9 by the reaction of excess diethylamine with 1.4;3.6-dianhydro-D-glucitol 5-methanesulphonate in butanol at 150°. Isolation as hydrogen nitrate.

M.p. 129° (from isopropanol); $[\alpha]_D^{25}$ 39.8 (c 1; water).

Elementary analysis: $C_{10}H_{19}NO_3 \times HNO_3$ (264.28); calc.: C (45.45), H (7.63), N (10.60); found: C (44.97), H (7.86), N (10.65).

EXAMPLE NO. 11

5-Pyrrolidino-5-desoxy-1.4;3.6-dianhydro-L-iditol

A mixture of 11.2 g. (50 mmol) 1.4;3.6-dianhydro-D-glucitol 5-methanesulphonate, 36 g. (0.5 mol) pyrrolidine and 100 ml. n-butanol is heated in a closed steel autoclave under a protective atmosphere of nitrogen for 24 hrs. at 150°. After cooling, one adds 10 ml. 5 molar aqueous sodium hydroxide solution thereto, evaporates off the excess pyrrolidine under reduced pressure—towards the end, with the addition of water—and extracts the product from the residue with chloroform. The evaporated chloroform extract is freed from insoluble by-products by dissolving in ether. The ether filtrate gives, after drying over anhydrous sodium sulphate and evaporation, 8.7 g. (43.7 mmol) 5-pyrrolidino-5-desoxy-1.4;3.6-dianhydro-L-iditol. For characterisation, a small portion is converted into the hydrogen nitrate and recrystallised from isopropanol.

M.p. 123°–4°; $[\alpha]_D^{25}$ 45.9 (c 1; ethanol).

Elementary analysis: $C_{10}H_{17}NO_3 \times HNO_3$ (262.26); calc.: C (45.80), H (6.92), N (10.68); found: C (45.74), H (7.16), N (10.79).

EXAMPLE NO. 12

5-Piperidino-5-desoxy-1.4;3.6-dianhydro-L-iditol

A mixture of 11.2 g. (50 mmol) 1.4;3.6-dianhydro-D-glucitol 5-methanesulphonate, 42.5 g. (0.5 mol) piperidine and 100 ml. n-butanol is heated for 24 hrs. in a closed steel autoclave under a nitrogen atmosphere to 150°. After evaporation under reduced pressure, one extracts the residue with ether, whereby piperidine hydrogen methanesulphonate remains undissolved. The ether extract, dried over anhydrous sodium sulphate, gives, after evaporation, 10 g. (47 mmol) of product, which is dissolved in 50 ml. acetic acid and converted into the hydrogen nitrate with the equimolar amount of 30% nitric acid. This is precipitated out with ether and, after recrystallisation from isopropanol, gives 11.6 g. (42 mmol) 5-piperidino-5-desoxy-1.4;3.6-dianhydro-L-iditol hydrogen nitrate.

M.p. 182°–4° (decomp.): $[\alpha]_D^{25}$ 46.0 (c 1; ethanol)

Elementary analysis: $C_{11}H_{19}NO_3 \times HNO_3$ (276.29); calc.: C (47.82), H (7.30), N (10.14); found: C (47.80), H (7.44), N (10.21).

EXAMPLE NO. 13

5-Morpholino-5-desoxy-1.4;3.6-dianhydro-L-iditol

Preparation analogously to Example 9 by reaction of 50 mmol 1.4;3.6-dianhydro-D-glucitol 5-methanesulphonate with 0.5 mol morpholine. Yield 8.6 g. (40 mmol) of oily product. Characterisation as hydrochloride.

M.p. 159°–161° (from isopropanol/ethanol) $[\alpha]_D^{25}$ 48.5 (c 1; ethanol).

Elementary analysis: $C_{10}H_{17}NO_4 \times HCl$ (251.71); calc.: C (47.72), H (7.21), N (5.57); found: C (47.42), H (7.20), N (5.61).

EXAMPLE NO. 14

5-(4-Methylpiperazino)-5-desoxy-1.4;3.6-dianhydro-L-iditol

A mixture of 11.2 g. (50 mmol) 1.4;3.6-dianhydro-D-glucitol 5-methanesulphonate and 15 g. (150 mmol) N-methylpiperazine is stirred under an atmosphere of nitrogen at 150° for 24 hrs. in a steel autoclave. After cooling, one adds thereto a solution of 2.0 g. (50 mmol) sodium hydroxide in 100 ml. n-butanol and evaporates to dryness under reduced pressure. The oily residue is treated with 500 ml. chloroform and filtered off from insolubles (sodium methanesulphonate). The chloroform phase is extracted 2 times with 200 ml. amounts of water; the combined aqueous phases give the crude base, after evaporation in vacuo and azeotropic drying with ethanol and chloroform. This is dissolved in 50 ml. glacial acetic acid and, by the addition of double the molar amount of dil. nitric acid, converted into the dihydrogen nitrate, the greater part of which crystallises out directly. Residual product is precipitated out with ether. Recrystallisation from isopropanol/ethanol gives 8.9 g. (25 mmol) 5-(4-methylpiperazino)-5-desoxy-1.4;3.6-dianhydro-L-iditol dihydrogen nitrate.

M.p. 124°–5° (decomp.): $[\alpha]_D^{25}$ 27.9 (c 0.5; water).

Elementary analysis: $C_{11}H_{20}N_2O_3 \times 2HNO_3$ (354.32); calc.: C (37.29), H (6.26), N (15.81); found: C (37.10), H (6.36), N (15.54).

EXAMPLE NO. 15

5-(9-Adenyl)-5-desoxy-1.4;3.6-dianhydro-L-iditol

Under an atmosphere of nitrogen and with stirring, one adds dropwise at 100° to a suspension of 15.7 g. (0.1 mol) adenine sodium salt in 200 ml. anhydrous dimethyl sulphoxide, a solution of 22.4 g. (0.1 mol) 1.4;3.6-dianhydro-D-glucitol 5-methanesulphonate in 100 ml. anhydrous dimethyl sulphoxide and further stirs for 8 days at 100°. One distils off the solvent in a vacuum and successively extracts the residue at boiling temperature with 100 ml. chloroform and n-butanol. The chloroform extract is concentrated to about 300 ml., the crude product is precipitated out by the addition of 600 ml. petroleum ether and separated off; the filtrate is discarded. The butanol extract gives further crude product after evaporation in a vacuum. The combined crude products are recrystallised from 400 ml. ethanol. One obtains 9.2 g. (35 mmol) 5-(9-adenyl)-5-desoxy-1.4;3.6-dianhydro-L-iditol. The evaporated mother liquor is dissolved in 200 ml. of water and continuously extracted with about 1 liter of a mixture of chloroform/butanol 9/1. Evaporation of the extract and recrystallisation from chloroform gives a further 3.9 g. (15 mmol) of pure product.

M.p. 202.5°–204.5°; $[\alpha]_D^{25}$ 22.2 (c 1; water).

Elementary analysis: $C_{11}H_{13}N_5O_3$ (263.25); calc.: C (50.19), H (4.98), N (26.60); found: C (50.39), H (5.04), N (26.69).

EXAMPLE NO. 16

5-(9-Adenyl)-5-desoxy-1.4;3.6-dianhydro-L-iditol (a) 5-(9-Adenyl)-5-desoxy-1.4;3.6-dianhydro-L-iditol 2-methanesulphonate:

A mixture of 20.15 g. (150 mmol) adenine sodium salt, 30.2 g. (100 mmol) 1.4;3.6-dianhydro-D-glucitol 2,5-dimethanesulphonate and 300 ml. dimethyl sulphoxide is heated for 24 hours to 100°, with stirring. After cooling, one mixes with 600 ml. of water, filters off with suction the precipitate consisting of reaction product and unreacted dimethanesulphonate and then washes twice with 50 ml. amounts of water. The precipitate is stirred with 600 ml. chloroform, whereby the dimethanesulphonate goes into solution and pure product remains behind. One obtains further product by extraction of the chloroform phase twice with 100 ml. amounts of 2 molar hydrochloric acid, neutralisation of the hydrochloric acid phases with dil. aqueous sodium hydroxide solution and suction filtration of the thereby resulting precipitate. Subsequently, one recrystallises from ethanol and obtains 17.5 g. (51.3 mmol) 5-(9-adenyl)-5-desoxy-1.4;3.6-dianhydro-L-iditol 2-methanesulphonate of m.p. 238°–240°; $[\alpha]_D^{25}$ 39.8 (c 1; dimethylformamide).

Elementary analysis: $C_{12}H_{15}N_5O_5S$ (341.34); calc.: C (42.22), H (4.43), N (20.52), S (9.39); found: C (42.36), H (4.34), N (20.76), S (9.2).

(b) 5-(9-Adenyl)-5-desoxy-1.4;3.6-dianhydro-L-iditol:

To a mixture, boiling under reflux, of 87 g. (255 mmol) 5-(9-adenyl)-5-desoxy-1.4;3.6-dianhydro-L-iditol 2-methanesulphonate and 4 liters of water, one adds dropwise with stirring, at a rate of 10 ml./hour, a solution of 30.6 g. (765 mmol) sodium hydroxide in 250 ml. water and subsequently further stirs for 5 hours under reflux. After cooling, one neutralises the solution with 510 mmol hydrochloric acid, evaporates in a vacuum, dries the residue azeotropically with n-butanol and boils it out three times with 2 liter amounts of n-butanol. The butanol extracts are evaporated in a vacuum and recrystallised from ethanol. One obtains 41.5 g. (158 mmol) 5-(9-adenyl)-5-desoxy-1.4;3.6-dianhydro-L-iditol of m.p. 203°. One obtains a further 10 g. (38 mmol) of product by evaporation of the mother liquor, extraction of the residue with chloroform and evaporation of the chloroform extract.

EXAMPLE NO. 17

5-(6-Methylmercaptopurin-9-yl)-5-desoxy-1.4;3.6-dianhydro-L-iditol

A solution of 166 g. (1 mol) 6-methylmercaptopurine and 40 g. (1 mol) sodium hydroxide in 1 liter of methanol is evaporated in a vacuum and dried to constant weight at 140°. One obtains 188 g. (1 mol) 6-methylmercaptopurine 9-sodium salt. These are suspended, together with 224 g. (1 mol) 1.4;3.6-dianhydro-D-glucitol 5-methanesulphonate, in 3 liters of dimethylformamide and heated for 24 hours to 130°, with stirring and under an atmosphere of nitrogen. Subsequently, one distils off the dimethylformamide in a vacuum, takes up the residue in 2 liters of water and extracts continuously in a rotary perforator with about 5 liters of chloroform. The chloroform extract is clarified over anhydrous sodium sulphate, filtered and evaporated. The remaining oily reaction product solidifies upon triturating with some water to give a crystalline slurry which is stirred with 600 ml. water, filtered off with suction and washed 2 times with 75 ml. of water. Subsequently, one dries in a vacuum drying cabinet at 120° to constant weight and obtains 147 g. (0.5 mol) 5-(6-methylmercaptopurin-9-yl)-5-desoxy-1.4;3.6-dianhydro-L-iditol. For analysis, one recrystallises from chloroform/toluene.

M.p. 146°–8°; $[\alpha]_D^{25}$ 22.5 (c 1; chloroform). Elementary analysis: $C_{12}H_{14}N_4O_3S$ (294.33); calc.: C (48.97), H (4.79), N (19.04), S (10.89); found: C (48.66), H (4.70), N (18.70), S (10.6).

EXAMPLE NO. 18

5-(6-Methylaminopurin-9-yl)-5-desoxy-1.4;3.6-dianhydro-L-iditol

A mixture of 8.8 g. (30 mmol) 5-(6-methylmercaptopurin-9-yl)-5-desoxy-1.4;3.6-dianhydro-L-iditol, 8.5 ml. of 33% methanolic methylamine solution (90 mmol) and 100 ml. water is stirred at 130° for 20 hours in a closed autoclave. After cooling and decompressing, one evaporates to dryness, dissolves the residue in 50 ml. water and extracts continuously with chloroform. Evaporation of the chloroform extract, dried over anhydrous sodium sulphate, gives 7.1 g. (25.6 mmol) of oily crude product which, for purification, is converted into the hydrochloride and recrystallised from methanol.

M.p. 247°–250° (decomp.); $[\alpha]_D^{25}$ 35.9 (c 1; water).
Elementary analysis: $C_{12}H_{15}N_5O_3xHCl$ (313.74); calc.: C (45.94), H (5.14), N (22.32), Cl (11.30); found: C (46.08), H (5.25), N (22.29), Cl (11.3).

EXAMPLE NO. 19

5-(6-Dimethylaminopurin-9-yl)-5-desoxy-1.4;3.6-dianhydro-L-iditol

A mixture of 8.8 g. (30 mmol) 5-(6-methylmercaptopurin-9-yl)-5-desoxy-1.4;3.6-dianhydro-L-iditol and 50 ml. of 40% aqueous dimethylamine solution is stirred in a closed autoclave for 20 hours at 130°. After cooling and decompressing, one evaporates in a vacuum and recrystallises from 20 ml. ethanol. One obtains 5.68 g. (19.5 mmol) 5-(6-dimethylaminopurin-9-yl)-5-desoxy-1.4;3.6-dianhydro-L-iditol. The analytical sample is recrystallised from toluene.

M.p. 139°–141°; $[\alpha]_D^{25}$ 29.5 (c 1; chloroform).

Elementary analysis: $C_{13}H_{17}N_5O_3$ (291.31); calc.: C (53.60), H (5.88), N (24.04); found: C (53.90), H (5.97), N (24.11).

EXAMPLE NO. 20

5-(6-Ethylaminopurin-9-yl)-5-desoxy-1.4;3.6-dianhydro-L-iditol

A mixture of 8.8 g. (30 mmol) 5-(6-methylmercaptopurin-9-yl)-5-desoxy-1,4;3.6-dianhydro-L-iditol, 8.1 g. (100 mmol) ethylamine hydrochloride, 4.0 g. (100 mmol) sodium hydroxide and 50 ml. water is stirred in a closed autoclave for 20 hours at 130°. After cooling and decompressing, one evaporates to dryness, dissolves the residue in 100 ml. water and extracts 10 times with 100 ml. amounts of chloroform. Evaporation of the chloroform extracts gives 8.15 g. of oily crude product which is converted into the hydrochloride with 14 ml. 2 molar hydrochloric acid, again evaporated and recrystallised from methanol/ether. One obtains 5.7 g. (17.4 mmol) 5-(6-ethylaminopurin-9-yl)-5-desoxy-1.4;3.6-dianhydro-L-iditol hydrochloride.

M.p. 240°–2°; $[\alpha]_D^{25}$ 37.7 (c 1; water).
Elementary analysis: $C_{23}H_{17}N_5O_3xHCl$ (327.76); calc.: C (47.64), H (5.53), N (21.37), Cl (10.82); found: C (47.78), H (5.61), N (21.40), Cl (10.95).

EXAMPLE NO. 21

5-(6-Pyrrolidinopurin-9-yl)-5-desoxy-1.4;3.6-dianhydro-L-iditol

A mixture of 8.8 g. (30 mmol) 5-(6-methylmercaptopurin-9-yl)-5-desoxy-1.4;3.6-dianhydro-L-iditol and 25 ml. (300 mmol) pyrrolidine is stirred for 20 hours in a closed autoclave at 130°. After cooling and decompressing, one distils off excess pyrrolidine, towards the end with the addition of water, and recrystallises the residue from water. One obtains 8.43 g. (26.6 mmol) 5-(6-pyrrolidinopurin-9-yl)-5-desoxy-1.4;3.6-dianhydro-L-iditol.

M.p. 183.5°–185.5°; $[\alpha]_D^{25}$ 34.5 (c 1; chloroform).
Elementary analysis: $C_{15}H_{19}N_5O_3$ (317.35); calc.: C (56.77), H (6.03), N (22.07); found: C (57.00), H (6.07), N (22.08).

EXAMPLE NO. 22

5-(6-Piperidinopurin-9-yl)-5-desoxy-1,4;3.6-dianhydro-L-iditol

Analogously to the preceding Example, 8.8 g. (30 mmol) 5-(6-methylmercaptopurin-9-yl)-5-desoxy-1.4;3.6-dianhydro-L-iditol, together with 25 ml. (253 mmol) piperidine, are stirred for 20 hours at 130° in a closed autoclave. After distilling off the excess piperidine (towards the end, with the addition of water), one triturates the oily residue with toluene. The now solid crude product is filtered off with suction, dried and recrystallised from water. One obtains 7.7 g. (23.2 mmol) of pure 5-(6-piperidinopurin-9-yl)-5-desoxy-1.4;3.6-dianhydro-L-iditol.

M.p. 136°–139°; $[\alpha]_D^{25}$ 30.1 (c 1; chloroform).
Elementary analysis: $C_{16}H_{21}N_5O_3$ (331.38); calc.: C (57.99), H (6.39), N (21.13); found: C (58.14), H (6.48), N (21.13).

EXAMPLE NO. 23

5-(6-Morpholinopurin-9-yl)-5-desoxy-1.4;3.6-dianhydro-L-iditol

Analogously to the preceding Examples 21 and 22, one obtains from 8.8 g. (30 mmol) 5-(6-methylmercaptopurin-9-yl)-5-desoxy-1.4;3.6-dianhydro-L-iditol and 25 ml. (287 mmol) morpholine, after stirring for 20 hours at 130° in a closed autoclave, distilling off of the excess morpholine, with the addition of water, and recrystallisation of the residue from water, 6.9 g. (18.7 mmol) of pure 5-(6-morpholinopurin-9-yl)-5-desoxy-1.4;3.6-dianhydro-L-iditol in the form of the dihydrate.

M.p. 84°–88°; $[\alpha]_D^{25}$ 26.4 (c 1; chloroform).

Elementary analysis: $C_{15}H_{19}N_5O_4 \times 2H_2O$ (369.38); calc.: C (48.78), H (6.28), N (18.96); found: C (48.71), H (6.31), N (18.74).

EXAMPLE NO. 24

5-[6-(4-Methylpiperazino)-purin-9-yl]-5-desoxy-1.4;3.6-dianhydro-L-iditol

Analogously to the preceding Examples, one obtains from 8.8 g. (30 mmol) 5-(-6-methylmercaptopurin-9-yl)-5-desoxy-1.4;3.6-dianhydro-L-iditol and 25 ml. (225 mmol) N-methylpiperazine, 10.2 g. (29.4 mmol) of crude product. Recrystallisation from toluene gives 6.3 g. (18.2 mmol) of pure product.

M.p. 166°–7°; $[\alpha]_D^{25}$ 31.1 (c 1, chloroform).

Elementary analysis: $C_{16}H_{22}N_6O_3$ (346.40); calc.: C (55.48), H (6.40), N (24.26); found: C (55.60), H (6.45), N (23.91).

EXAMPLE NO. 25

5-(6-Benzylaminopurin-9-yl)-5-desoxyl-1.4;3.6-dianhydro-L-iditol

A mixture of 8.8 g. (30 mmol) 5-(6-methylmercaptopurin-9-yl)-5-desoxy-1.4;3.6-dianhydro-L-iditol and 25 ml. (229 mmol) benzylamine is stirred in a closed autoclave for 20 hrs. at 130°. After cooling and decompressing, one distils off the excess benzylamine in a vacuum—towards the end, with the addition of water—recrystallises the oily residue from acetone and obtains 6.9 g. (19.5 mmol) 5-(6-benzylaminopurin-9-yl)-5-desoxy-1.4;3.6-dianhydro-L-iditol. The analytical sample is again recrystallised from toluene.

M.p. 151°–3°; $[\alpha]_D^{25}$ 28.7 (c 1; chloroform).

Elementary analysis: $C_{18}H_{19}N_5O_3$ (353.38); calc.: C (61.18), H (5.42), N (19.82); found: C (61.17), H (5.44), N (19.82).

EXAMPLE NO. 26

5-[6-(3-Phenylpropyl)-aminopurin-9-yl]-5-desoxy-1.4;3.6-dianhydro-L-iditol

A mixture of 19.1 g. (65 mmol) 5-(6-methylmercaptopurin-9-yl)-5-desoxy-1.4;3.6-dianhydro-L-iditol and 94 ml. (650 mmol) 3-phenylpropylamine is heated in a closed steel autoclave for 36 hrs. at 150°. After cooling and decompressing, one adds 80 ml. acetic acid and 500 ml. water thereto and extracts twice with 300 ml. amounts of chloroform. The chloroform extracts are washed with a solution of 25 ml. 37% hydrochloric acid in 200 ml. water. The hydrochloric acid extracts are rendered alkaline with aqueous sodium hydroxide solution and extracted with 400 ml. dichloromethane. The dichloromethane extract gives, after drying over anhydrous sodium sulphate, filtering and evaporating, 20 g. (52.4 mmol) of crude base which is dissolved, with warming, in 150 ml. isopropanol and mixed with 15 ml. 37% hydrochloric acid (180 mmol). Upon cooling, 18.8 g. (41.4 mmol) of pure product crystallise out in the form of the dihydrochloride.

M.p. 159°–62°; $[\alpha]_D^{25}$ 30.6 (c 0.4; water).

Elementary analysis: $C_{20}H_{23}N_5O_3 \times HCl$ (454.36); calc.: C (52.86), H (5.55), N (15.41), Cl (15.61); found: C (53.23), H (5.55), N (15.41), Cl (14.4).

EXAMPLE NO. 27

5-[6-(2-phenylethyl)-aminopurin-9-yl]-5-desoxy-1.4;3.6-dianhydro-L-iditol

Preparation analogously to Example 26 by the reaction of 5-(6-methylmercaptopurin-9-yl)-5-desoxy-1.4;3.6-dianhydro-L-iditol with excess 2-phenylethylamine at 130°. Isolation as hydrochloride. Yield, after recrystallisation from ethanol: 58%. M.p. 214°–18°; $[\alpha]_D^{25}$ 32.7 (c 0.39; water).

Elementary analysis: $C_{19}H_{21}N_5O_3 \times HCl$ (403.87); calc.: C (56.51), H (5.49), N (17.34), Cl (8.78); found: C (56.42), H (5.87), N (17.39), Cl (9.1).

EXAMPLE NO. 28

5-[6-(4-Phenylbutyl)-aminopurin-9-yl]-5-desoxy-1.4;3.6-dianhydro-L-iditol

Preparation analogously to Example 26 by the reaction of 5-(6-methylmercaptopurin-9-yl)-5-desoxy-1.4;3.6-dianhydro-L-iditol with excess 4-phenylbutylamine at 150°. Isolation as hydrochloride. Yield, after recrystallisation from isopropanol: 47%.

M.p. 172°–6°; $[\alpha]_D^{25}$ 30.6 (c 0.4; water).

Elementary analysis: $C_{21}H_{25}N_5O_3 \times HCl$ (431.92); calc.: C (58.40), H (6.07), N (16.21), Cl (8.21); found: C (58.15), H (6.15), N (15.94), Cl (8.5).

EXAMPLE NO. 29

2-(9-Adenyl)-2-desoxy-1.4;3.6-dianhydro-D-glucitol

A mixture of 112 g. (0.5 mol) 1.4;3.6-dianhydro-D-mannitol 2-methanesulphonate (prepared according to Example 4a), 86 g. (0.55 mol) adenine sodium salt and 1500 ml. anhydrous dimethyl sulphoxide is stirred for 24 hrs. under an atmosphere of nitrogen at 120°. One distils off the dimethyl sulphoxide under reduced pressure, dissolves the residue in 1 liter of water, extracts lipophilic by-products 2 times with 300 ml. amounts of chloroform and concentrates the aqueous phase to about 200 ml. The crude product which crystallises out gives, after recrystallisation from ethanol/water, 47.4 g. (0.18 mol) 2-(9-adenyl)-2-desoxy-1.4;3.6-dianhydro-D-glucitol.

M.p. 265°–7°; $[\alpha]_D^{25}$ 20.8 (c 1.0; water).

Elementary analysis: $C_{11}H_{13}N_5O_3$ (263.25); calc.: C (50.19), H (4.98), N (26.60); found: C (49.97), H (5.04), N (26.80).

EXAMPLE NO. 30

5-(7-Theophyllinyl)-5-desoxy-1.4;3.6-dianhydro-L-iditol a mixture of 44.8 g. (0.2 mol) 1.4;3.6-dianhydro-D-glucitol 5-methanesulphonate, 80.8 g. (0.4 mol) theophylline sodium salt and 600 ml. dimethyl sulphoxide is stirred for 48 hours under an atmosphere of nitrogen at 130°. One distils off the dimethyl sulphoxide in a vacuum, dissolves the residue in 400 ml. hot water, extracts, after cooling, twice with 200 ml. amounts of chloroform and shakes out the chloroform extracts with 200 ml. water. The combined aqueous phases are boiled up with 30 g. active charcoal, filtered and the filtrate, after neutralisation, evaporated to dryness. The residue is stirred with 1 liter ethanol, filtered and again evaporated. For the removal of residual theophylline, one then dissolves in 700 ml. 2% aqueous sodium hydroxide solution and extracts the reaction product continuously with chloroform. The chloroform extract gives, after drying over anhydrous sodium sulphate and evaporation, 27.5 g. (89 mmol) 5-(7-theophyllinyl)-5-desoxy-1.4;3.6-dianhydro-L-iditol. The analytical sample is recrystallised from acetone/ethanol.

M.p. 196°-8°; $[\alpha]_D^{25}$ −27.9 (c 0.5; water).

Elementary analysis: $C_{13}H_{16}N_4O_5$ (308.30); calc.: C (50.65), H (5.23), N (18.17); found: C (50.68), H (5.32), N (18.06).

EXAMPLE NO. 31

5-(2-Theophyllin-7-ylethylamino)-5-desoxy-1.4;3.6-dianhydro-L-iditol

A mixture of 8.6 g. (30 mmol) 7-(2-bromoethyl)theophylline, 8 ml. ethanol and 10.8 g. (75 mmol) 5-amino-5-desoxy-1.4;3.6-dianhydro-L-iditol (preparation see Examples 1 and 2) is boiled under reflux for 24 hrs. and then evaporated under reduced pressure. The residue is dissolved in 100 ml. water and extracted 10 times with 100 ml. amounts of chloroform, whereby the first chloroform extract is discarded. The chloroform extracts 2–10 are evaporated under reduced pressure. Conversion of the residue into the hydrochloride and recrystallisation from methanol give 7.93 g. (20.4 mmol) 5-(2-theophyllin-7-ylethylamino)-5-desoxy-1.4;3.6-dianhydro-L-iditol hydrochloride.

M.p. 216°-221°; $[\alpha]_D^{25}$ 34.1 (c 0.39; water).

Elementary analysis: $C_{15}H_{21}N_5O_5 \times HCl$ (387.83); calc.: C (46.46), H (5.72), N (18.06), Cl (9.14); found: C (46.25), H (5.99), N (17.46), Cl (9.5).

EXAMPLE NO. 32

5-(3-Theophyllin-7-ylpropylamino)-5-desoxy-1.4;3.6-dianhydro-L-iditol

To a solution, boiling under reflux, of 109 g. (0.75 mol) 5-amino-5-desoxy-1.4;3.6-dianhydro-L-iditol in 1 liter ethanol, one adds, via a Soxhlet extractor cup, within 10 hrs., 75.3 g. (0.25 mol) 7-(3-bromopropyl)-theophylline, then boils for 48 hrs. and evaporates under reduced pressure. The residue is dissolved in 1.5 liters of water, brought to pH=4 with hydrochloric acid, washed with 500 ml. chloroform, then adjusted with sodium hydroxide to pH 8.5 and continuously extracted with chloroform in a rotary perforator (Normag) until all the reaction product has passed over into the chloroform phase. The chloroform extract is evaporated under reduced pressure, dissolved in isopropanol, converted into the hydrogen methanesulphonate by the addition of methanesulphonic acid and, after evaporation, recrystallised from ethanol/isopropanol. One obtains 83.5 g. (0.18 mol) 5-(3-theophyllin-7-ylpropylamino)-5-desoxy-1.4;3.6-dianhydro-L-iditol hydrogen methanesulphonate.

M.p. 145°-147°; $[\alpha]_D^{25}$ 24.2 (c 0.5; water).

Elementary analysis: $C_{16}H_{23}N_5O_5 \times CH_3SO_3H$ (461.50); calc.: C (44.24), H (5.90), N (15.17), S (6.95); found: C (44.11), H (5.92), N (15.03), S (7.2).

The aqueous phase of the perforation is evaporated under reduced pressure, extracted with ethanol, filtered and evaporated, the evaporation residue extracted with chloroform, filtered and again evaporated. This residue gives, after extraction with n-butanol, filtering, evaporating and drying in a vacuum drying cabinet at 80°, 59 g. (406 mmol 81%) of the excess 5-amino-5-desoxy-1.4;3.6-dianhydro-L-iditol.

EXAMPLE NO. 33

5-(4-Theophyllin-7-ylbutylamino)-5-desoxy-1.4;3.6-dianhydro-L-iditol

Preparation analogously to Example 32 by the reaction of 7-(4-bromobutyl)-theophylline with excess 5-amino-5-desoxy-1.4;3.6-dianhydro-L-iditol, with the addition of potassium iodide. Isolation as hydrochloride. Yield, after recrystallisation from isopropanol/chloroform: 44%.

M.p. 196°-8°; $[\alpha]_D^{25}$ 29.8 (c 0.41; water).

Elementary analysis: $C_{17}H_{25}N_5O_5 \times HCl$ (415.88); calc.: C (49.10), H (6.30), N (16.84), Cl (8.52); found: C (48.77), H (6.56), N (16.57), Cl (8.6).

EXAMPLE NO. 34

5-(5-Theophyllin-7-ylpentylamino)-5-desoxy-1.4;3.6-dianhydro-L-iditol

Preparation analogously to Example 33 by the reaction of 7-(5-bromopentyl)-theophylline with excess 5-amino-5-desoxy-1.4;3.6-dianhydro-L-iditol. Isolation as hydrochloride. Yield, after recrystallisation from ethanol/chloroform: 69%.

M.p. 230°-233°; $[\alpha]_D^{25}$ 28.9 (c 0.4; water).

Elementary analysis: $C_{18}H_{27}N_5O_5 \times HCl$ (429.90); calc.: C (50.29), H (6.56), N (16.29), Cl (8.25); found: C (50.40), H (6.69), N (16.38), Cl (8.3).

EXAMPLE NO. 35

5-(6-Theophyllin-7-ylhexylamino)-5-desoxy-1.4;3.6-dianhydro-L-iditol

Preparation analogously to Example 33 by the reaction of 7-(6-bromohexyl)-theophylline with excess 5-amino-5-desoxy-1.4;3.6-dianhydro-L-iditol. Isolation as hydrochloride. Yield, after recrystallisation from chloroform/acetone: 39%.

M.p. 180°-183°; $[\alpha]_D^{25}$ 27.1 (c 0.4; water).

Elementary analysis: $C_{19}H_{29}N_5O_5 \times HCl$ (443.93) calc.: C (51.41), H (6.81), N (15.78), Cl (7.99) found: C (51.12), H (6.90), N (15.59), Cl (8.6)

EXAMPLE NO. 36

5-(4-Theophyllin-7-yl-2-butylamino)-5-desoxy-1.4;3.6-dianhydro-L-iditol

To a solution of 10 g. (40 mmol) 7-(3-oxobutyl)theophylline in 75 ml. ethanol, one adds a solution of 5.8 g. (40 mmol) 5-amino-5-desoxy-1.4;3.6-dianhydro-L-iditol in 40 ml. methanol, adds thereto a suspension of 1.5 g. 10% Pd/C catalyst in 100 ml. ethanol, flushes with nitrogen and hydrogenates in a closed steel autoclave under 50 ats. hydrogen pressure for 20 hrs. at room temperature and for 8 hrs. at 50°, whereby one shakes about 250 times/min. After cooling, decompressing and filtering off the catalyst, one evaporates the filtrate under reduced pressure, adjusts the solution of the residue in water to pH=2 with hydrochloric acid and perforates for 8 hrs. in a rotary perforator with chloroform in order to extract by-products. One adjusts the aqueous phase to pH=4 and again perforates with chloroform. Both chloroform phases are discarded. After adjustment to pH=7, one perforates for 8 hrs. with chloroform. From this chloroform phase, one obtains, after drying over anhydrous sodium sulphate and evaporating under reduced pressure, 8.5 g. (22.4 mmol) 5-(4-theophyllin-7-yl-2-butylamino-5-desoxy-1.4;3.6-dianhydro-L-iditol (mixture of the two epimers) in the form of a colourless oil. For analysis, one converts into the hydrochloride and reprecipitates from isopropanol with pentane.

M.p. 155°-156° (decomp.); $[\alpha]_D^{25}$ 6.7 (c 0.39; water).

Elementary analysis: $C_{17}H_{25}N_5O_5xHCl$ (415.88); calc.: C (49.10), H (6.30), N (16.84), Cl (8.52); found: C (49.11), H (6.48), N (16.28), Cl (8.5).

EXAMPLE NO. 37

5-Theophyllin-7-yl-5-desoxy-1.4;3.6-dianhydro-L-iditol 2-methanesulphonate

A mixture of 36 g. (178 mmol) theophylline sodium, 36 g. (120 mmol) 1.4;3.6-dianhydro-D-glucitol 2,5-dimethanesulphonate and 500 ml. anhydrous diethylene glycol diethyl ether is stirred for 2 days with the exclusion of moisture at 180°. One filters, evaporates the filtrate under reduced pressure, mixes the residue with 800 ml. water, filters and extracts 3 times with 600 ml. amounts of chloroform. The chloroform phases are, after washing with 200 ml. 2 molar aqueous sodium hydroxide solution and drying over anhydrous sodium sulphate, concentrated to a volume of about 200 ml. and the crude product precipitated out by the addition of petroleum ether. The precipitate is dissolved in boiling chloroform. Upon cooling, unreacted 1.4;3.6-dianhydro-D-glucitol 2,5-dimethanesulphonate crystallises out and is filtered off with suction. By the renewed addition of petroleum ether, from the filtrate one precipitates out 24.3 g. (63 mmol) 5-theophyllin-7-yl-5-desoxy-1.4;3.6-dianhydro-L-iditol 2-methanesulphonate which, after recrystallisation from ethanol, has the m.p. 191°-4°. $[\alpha]_D^{25}$ 17.2 (c 0.51; dimethylformamide).

Elementary analysis: $C_{14}H_{18}N_4O_7S$ (386.39); calc.: C (43.53), H (4.69), N (14.50), S (8.30); found: C (43.47), H (4.78), N (14.02), S (8.30).

EXAMPLE NO. 38

5-[6-(3-p-Chlorophenylpropyl)-aminopurin-9-yl]-5-desoxy-1.4;3.6-dianhydro-L-iditol Preparation analogously to Example 26 by the reaction of 5-(6-methylmercaptopurin-9-yl)-5-desoxy-1.4;3.6-dianhydro-L-iditol with excess 3-(4-chlorophenyl)propylamine in ethanol at 150° in a closed steel autoclave. Isolation as hydrochloride with ½ mole water of crystallisation. M.p. after recrystallisation from ethanol 116°-120°. $[\alpha]_D^{25}$ 22.5 (c 0.2; water).

Elementary analysis: $C_{20}H_{22}ClN_5O_3xHClx0.5H_2O$ (461.35); calc.: C (52.07), H (5.24), N (15.18), Cl (15.37); found: C (52.34), H (5.20), N (15.15), Cl (15.50).

EXAMPLE NO. 39

2-(7-Theophyllinyl)-2-desoxy-1.4;3.6-dianhydro-D-glucitol

Preparation analogously to Example No. 30 by the reaction of 1.4;3.6-dianhydro-D-mannitol 2-methanesulphonate with theophylline potassium in anhydrous dimethyl sulphoxide at 120°. After recrystallisation from methanol/water, one obtains pure 2-(7-theophyllinyl)-2-desoxy-1.4;3.6-dianhydro-D-glucitol with m.p. 230°-31° C. and $[\alpha]_D^{25}$ —27.3 (c 0.4; water).

Elementary analysis: $C_{13}H_{16}N_4O_5$ (308.30); calc.: C (50.65), H (5.23), N (18.17); found: C (50.69), H (5.26), N (17.96).

EXAMPLE NO. 40

2-(7-Theophyllinyl)-2-desoxy-1.4;3.6-dianhydro-D-glucitol 5-methanesulphonate

A mixture of 150 g. (0.5 mol) 1.4;3.6-dianhydro-D-mannitol 2,5-dimethanesulphonate, 87 g. (0.4 mol) theophylline potassium and 1500 ml. anhydrous dimethyl sulphoxide is stirred for 68 hrs. at 110° C. in a closed steel autoclave under an atmosphere of nitrogen. After substantially distilling off of the dimethyl sulphoxide under reduced pressure, one stirs the residue with 500 ml. water and 200 ml. chloroform, filters off the precipitate (N 1) with suction, separates the chloroform phase (C) from the filtrate and discards the aqueous phase.

N 1 is stirred with 400 ml. water, suction filtered, dried, boiled up with 200 ml. dichloromethane, after cooling left to stand for 2 hrs. and again filtered off with suction. One obtains almost pure product (N 2).

The chloroform solution C is evaporated and boiled up with 200 ml. acetone. The disubstitution product which precipitates out on cooling is separated off, the filtrate is evaporated and recrystallised from dichloromethane. The crystallisate (N 3) is combined with N 2 and recrystallised from acetone. One obtains 44.6 g. (115 mmol) of pure 2-(7-theophyllinyl)-2-desoxy-1.4;3.6-dianhydro-D-glucitol 5-methanesulphonate with m.p. 200°-203° C. and $[\alpha]_D^{25}$ 31.3 (c 0.40; dimethylformamide).

Elementary analysis: $C_{14}H_{18}N_4O_7S$ (386.39); calc.: C (43.52), H (4.69), N (14.50), S (8.30); found: C (43.29), H (4.81), N (14.07), S (8.2).

Recrystallisation of the disubstitution product from 96% ethanol gives pure 2,5-bis-(7-theophyllinyl)-2,5-didesoxy-1.4;3.6-dianhydro-L-iditol in the form of the hemihydrate with m.p. 303°-305° (decomp.) and $[\alpha]_D^{20}$ —61.5 (c 0.4; dimethylformamide).

Elementary analysis: $C_{20}H_{22}N_8O_6x0.5H_2O$ (479.45); calc.: C (50.10), H (4.83), N (23.37); found: C (50.36), H (4.61), N (23.28).

EXAMPLE NO. 41

2-(7-Theophyllinyl)-2-desoxy-1.4;3.6-dianhydro-D-glucitol 5-p-toluenesulphonate

Preparation analogously to Example 40 by the reaction of 1.4;3.6-dianhydro-D-mannitol 2,5-di-p-toluenesulphonate with theophylline potassium in dimethyl sulphoxide. Recrystallisation from chloroform/ethanol gives pure product with m.p. 175°-176° and $[\alpha]_D^{20}$ 37.3 (c 0.4; dimethylformamide).

Elementary analysis: $C_{20}H_{22}N_4O_7S$ (462.49); calc.: C (51.94), H (4.80), N (12.11), S (6.93); found: C (52.07), H (5.02), N (12.20), S (7.0).

EXAMPLE NO. 42

2-Dimethylamino-2-desoxy-1.4;3.6-dianhydro-D-glucitol

A mixture of 45 g (0.2 mol) 1.4;3.6-dianhydro-D-mannitol 2-methanesulphonate and 150 ml. 40% aqueous dimethylamine solution is stirred for 18 hrs. under an atmosphere of nitrogen in a closed steel autoclave at 150° C. After cooling and decompressing, one adds 8.0 g. (0.2 mol) sodium hydroxide and 10 g. active charcoal thereto, boils under reflux for 15 min., filters, evaporates the filtrate and dries azeotropically with toluene. The residue is extracted with chloroform. Evaporation of the extract gives 25 g. (144 mmol) of slowly solidifying crude product. For purification, one converts into the hydrochloride and recrystallises twice from isopropanol. One obtains 2-dimethylamino-2-desoxy-1.4;3.6-dianhydro-D-glucitol hydrochloride with m.p. 175° C. and $[\alpha]_D^{20}$ 59.2 (c 0.5; water).

Elementary analysis: $C_8H_{15}NO_3 \times HCl$ (209.68); calc.: C (45.82), H (7.69), N (6.68), Cl (16.91); found: C (45.72), H (8.03), N (6.28), Cl (17.0).

I claim:

1. Aminodesoxy-1.4;3.6-dianhydrohexitol derivatives of the general formula

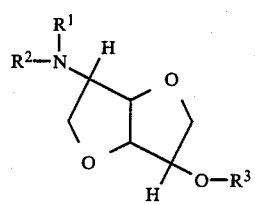

(I)

wherein $R^1$ and $R^2$, together with the nitrogen atom to which they are attached,
(a) signify the aden(9)yl radical possibly mono or disubstituted on the 6-amino group or
(b) the 6-alkylmercaptopurin(9)yl radical or
(c) the theophyllin(7)yl radical or
(d) the 6-chloropurin-9-yl radical or wherein
$R^1$ signifies a hydrogen atom or a lower alkyl group with 1 to 4 carbon atoms and
$R^2$ an ω-theophyllin(7)ylalkyl radical or an ω-theobromin-1-ylalkyl radical or an ω-(N,N'-di-lower alkyl-substituted xanthin-N''-yl)-alkyl radical, whereby lower alkyl signifies an alkyl group with 1 to 5 carbon atoms, or an ω-adenin-9-ylalkyl radical, whereby the alkyl radical has 2 to 7 carbon atoms and can be straight chained or branched, and wherein
$R^3$ signifies a hydrogen atom, a methanesulphonyl or toluenesulphonyl group,
as well as their acid addition salts.

2. 5-Amino-5-desoxy-1.4;3.6-dianhydro-L-iditol derivatives of the general formula V,

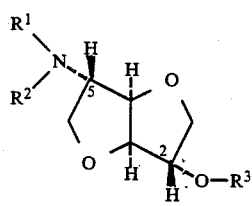

(V)

wherein $R^1$, $R^2$ and $R^3$ possess the meanings given in claim 1, as well as their acid-addition salts.

3. 5-Amino-5-desoxy-1.4;3.6-dianhydro-D-glucitol derivatives of the general formula VI,

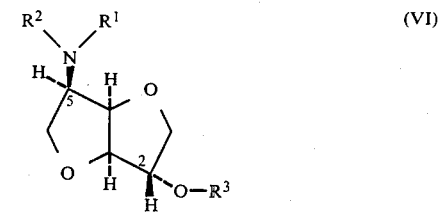

(VI)

wherein $R^1$, $R^2$ and $R^3$ possess the meanings given in claim 1, as well as their acid-addition salts.

4. 2-Amino-2-desoxy-1.4;3.6-dianhydro-D-glucitol derivatives of the general formula VII,

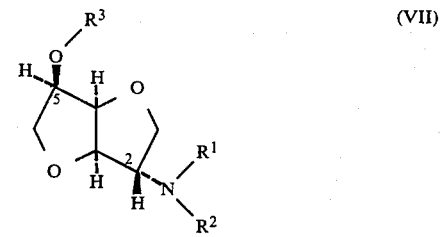

(VII)

wherein $R^1$, $R^2$ and $R^3$ possess the meanings given in claim 1, as well as their acid-addition salts.

5. 2-Amino-2-desoxy-1.4;3.6-dianhydro-D-mannitol derivatives of the general formula VIII,

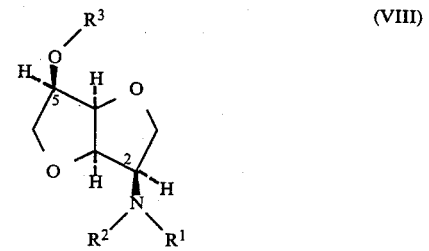

(VIII)

wherein $R^1$, $R^2$ and $R^3$ possess the meanings given in claim 1, as well as their acid-addition salts.

6. (Purin-9-yl)-desoxy-1.4;3.6-dianhydrohexitol derivatives of the general formula IX,

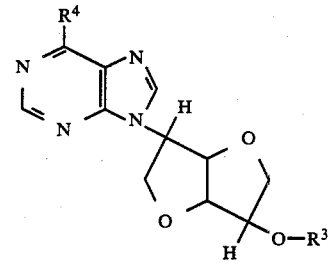

(IX)

wherein $R^3$ signifies a hydrogen atom, a methanesulphonyl or toluenesulphonyl group and $R^4$ an amino, alkylmercapto, alkylamino or dialkylamino group with 1 to 4 C-atoms, an ω-phenylalkylamino group, the alkyl radical of which has 1 to 8 C-atoms and the phenyl radical of which is possibly halogen-substituted or the residue of a cyclic, nonaromatic secondary amine possibly containing a further hetero atom, or is a chlorine atom, as well as their acid-addition salts.

7. 5-(Purin-9-yl)-5-desoxy-1.4;3.6-dianhydro-L-iditol derivatives of the general formula X,

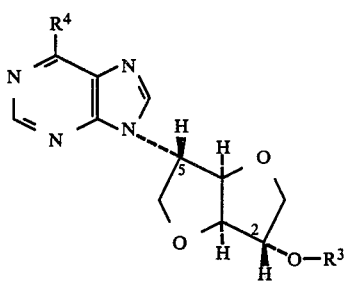

wherein R³ and R⁴ possess the meanings given in claim 6, as well as their acid-addition salts.

8. 5-(Purin-9-yl)-5-desoxy-1.4;3.6-dianhydro-D-glucitol derivatives of the general formula XI,

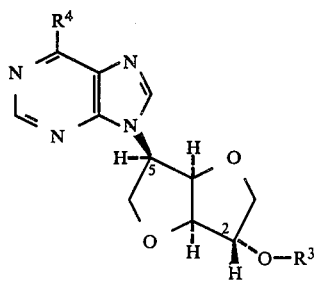

wherein R³ and R⁴ possess the meanings given in claim 6, as well as their acid-addition salts.

9. 2-(Purin-9-yl)-2-desoxy-1.4;3.6-dianhydro-D-glucitol derivatives of the general formula XII,

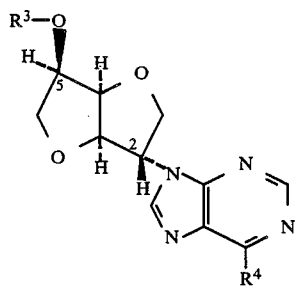

wherein R³ and R⁴ possess the meanings given in claim 6, as well as their acid-addition salts.

10. 2-(Purin-9-yl)-2-desoxy-1.4;3.6-dianhydro-D-mannitol derivatives of the general formula XIII,

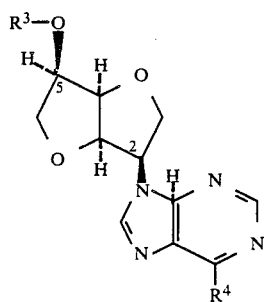

wherein R³ and R⁴ possess the meanings given in claim 6, as well as their acid-addition salts.

11. (Theophyllin-7-yl)-desoxy-1.4;3.6-dianhydrohexitol derivatives of the general formula XIV,

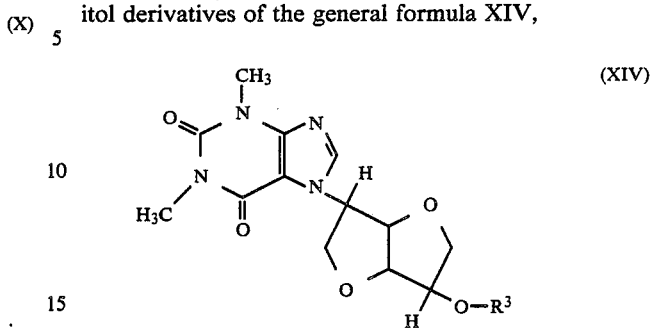

wherein R³ signifies a hydrogen atom, a methanesulphonyl or toluenesulphonyl group, as well as their acid-addition salts.

12. (ω-Purinylalkylamino)-desoxy-1.4;3.6-dianhydrohexitol derivatives of the general formula XV,

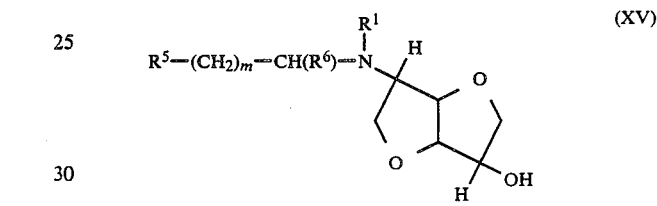

wherein R¹ signifies a hydrogen atom or a lower alkyl group with 1 to 4 C-atoms, R⁵ the adenin-9-yl radical, the theophyllin-7-yl radical, the theobromin-1-yl radical or a further N,N'-di-lower alkylxanthin-N''-yl radical, whereby "lower alkyl" means an alkyl group with 1 to 5 C-atoms, R⁶ signifies a hydrogen atom or a methyl group and m a whole number from 1 to 6, as well as their acid-addition salts.

13. ω-(Theophyllin-7-yl)-alkylamino-desoxy-1.4;3.6-dianhydro-hexitols of the general formula XVI,

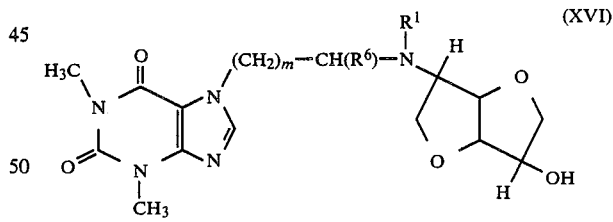

wherein R¹, R⁶ and m possess the meanings given in claim 12, as well as their acid-addition salts.

14. 5-(9-Adenyl)-5-desoxy-1.4;3.6-dianhydro-L-iditol.

15. 5-(9-Adenyl)-5-desoxy-1.4;3.6-dianhydro-L-iditol 2-methanesulphonate.

16. 5-(6-Methylmercaptopurin-9-yl)-5-desoxy-1.4;3.6-dianhydro-L-iditol.

17. 5-(6-Methylaminopurin-9-yl)-5-desoxy-1.4;3.6-dianhydro-L-iditol.

18. 5-(6-Dimethylaminopurin-9-yl)-5-desoxy-1.4;3.6-dianhydro-L-iditol.

19. 5-(6-Ethylaminopurin-9-yl)-5-desoxy-1.4;3.6-dianhydro-L-iditol.

20. 5-(6-Pyrrolidinopurin-9-yl)-5-desoxy-1.4;3.6-dianhydro-L-iditol.

21. 5-(6-Piperidinopurin-9-yl)-5-desoxy-1.4;3.6-dianhydro-L-iditol.

22. 5-(6-Morpholinopurin-9-yl)-5-desoxy-1.4;3.6-dianhydro-L-iditol.

23. 5-[6-(4-Methylpiperazino)-purin-9-yl]-5-desoxy-1.4;3.6-dianhydro-L-iditol.

24. 5-(6-Benzylaminopurin-9-yl)-5-desoxy-1.4;3.6-dianhydro-L-iditol.

25. 5-(6-p-Chlorobenzylaminopurin-9-yl)-5-desoxy-1.4;3.6-dianhydro-L-iditol.

26. 5-[6-(3-Phenylpropyl)-aminopurin-9-yl]-5-desoxy-1.4;3.6-dianhydro-L-iditol.

27. 5-[6-(3-p-Chlorophenylpropyl)-aminopurin-9-yl]-5-desoxy-1.4;3.6-dianhydro-L-iditol.

28. 5-[6-(2-Phenylethyl)-aminopurin-9-yl]-5-desoxy-1.4;3.6-dianhydro-L-iditol.

29. 5-[6-(2-p-Chlorophenylethyl)-aminopurin-9-yl]-5-desoxy-1.4;3.6-dianhydro-L-iditol.

30. 5-[6-(4-Phenylbutyl)-aminopurin-9-yl]-5-desoxy-1.4;3.6-dianhydro-L-iditol.

31. 5-[6-(4-p-Chlorophenylbutyl)-aminopurin-9-yl]-5-desoxy-1.4;3.6-dianhydro-L-iditol.

32. 2-(9-Adenyl)-2-desoxy-1.4;3.6-dianhydro-D-glucitol.

33. 5-(7-Theophyllinyl)-5-desoxy-1.4;3.6-dianhydro-L-iditol.

34. 5-Theophyllin-7-yl-5-desoxy-1.4;3.6-dianhydro-L-iditol 2-methanesulphonate.

35. 5-(2-Theophyllin-7-ylethylamino)-5-desoxy-1.4;3.6-dianhydro-L-iditol.

36. 5-(3-Theophyllin-7-ylpropylamino)-5-desoxy-1.4;3.6-dianhydro-L-iditol.

37. 5-(4-Theophyllin-7-ylbutylamino)-5-desoxy-1.4;3.6-dianhydro-L-iditol.

38. 5-(5-Theophyllin-7-ylpentylamino)-5-desoxy-1.4;3.6-dianhydro-L-iditol.

39. 5-(6-Theophyllin-7-ylhexylamino)-5-desoxy-1.4;3.6-dianhydro-L-iditol.

40. 5-(4-Theophyllin-7-yl-2-butylamino)-5-desoxy-1.4;3.6-dianhydro-L-iditol.

41. 2-(7-Theophyllinyl)-2-desoxy-1.4;3.6-dianhydro-D-glucitol.

42. 2-(7-Theophyllinyl)-2-desoxy-1.4;3.6-dianhydro-D-glucitol 5-methanesulphonate.

43. 2-(7-Theophyllinyl)-2-desoxy-1.4;3.6-dianhydro-D-glucitol 5-p-toluenesulphonate.

* * * * *